(12) United States Patent
Daikuzono

(10) Patent No.: US 6,221,069 B1
(45) Date of Patent: Apr. 24, 2001

(54) APPARATUS FOR MEDICAL TREATMENT

(75) Inventor: Norio Daikuzono, Cincinnati, OH (US)

(73) Assignee: S.L.T. Japan Co., Ltd., Tokyo (JP)

( * ) Notice: Subject to any disclaimer, the term of this patent is extended or adjusted under 35 U.S.C. 154(b) by 0 days.

(21) Appl. No.: 08/978,598

(22) Filed: Nov. 25, 1997

(30) Foreign Application Priority Data

Nov. 26, 1996 (JP) .................................................. 8-314675

(51) Int. Cl.[7] .................................................. A61B 18/04
(52) U.S. Cl. .................................. 606/28; 606/13; 606/16
(58) Field of Search .......................... 606/45, 46, 48–50, 606/28; 607/89

(56) References Cited

U.S. PATENT DOCUMENTS

| 4,249,533 | * | 2/1981 | Komiya . | |
|---|---|---|---|---|
| 4,985,030 | | 1/1991 | Melzer et al. . | |
| 5,328,488 | | 7/1994 | Daikuzono . | |
| 5,342,358 | * | 8/1994 | Daikuzono | 606/45 |
| 5,366,476 | * | 11/1994 | Noda | 606/206 |
| 5,460,629 | * | 10/1995 | Shlain et al. | 606/46 |
| 5,470,331 | | 11/1995 | Daikuzono . | |
| 5,611,798 | | 3/1997 | Eggers . | |
| 5,669,922 | | 9/1997 | Hood . | |
| 5,674,191 | | 10/1997 | Edwards et al. . | |

FOREIGN PATENT DOCUMENTS

| 0 669 107 A1 | 8/1995 | (EP) . |
|---|---|---|
| 3-218742 | 6/1991 | (JP) . |
| WO 92 06641 | 4/1992 | (WO) . |

* cited by examiner

Primary Examiner—Linda C. M. Dvorak
Assistant Examiner—Roy Gibson
(74) Attorney, Agent, or Firm—McDermott, Will & Emery

(57) ABSTRACT

The present invention relates to an apparatus for medical treatment and in particular to an apparatus for medical treatment which is miniaturized to such a size that it can be used together with an endoscope and is capable of incising living tissue with less bleeding. The apparatus for medical treatment is characterized in that said apparatus includes: an outer probe which is in a form of hook; an inner probe which faces said outer probe and is capable of being in and out of contact with said inner probe in a longitudinal direction by the operator's actuation; and heating means for heating a target tissue to be treated which is disposed between said outer and inner probes.

5 Claims, 23 Drawing Sheets

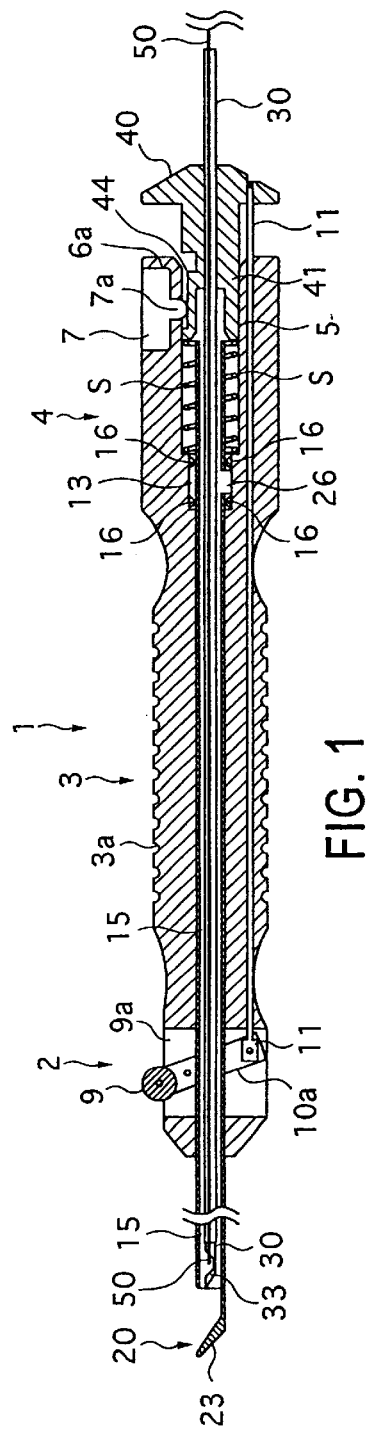
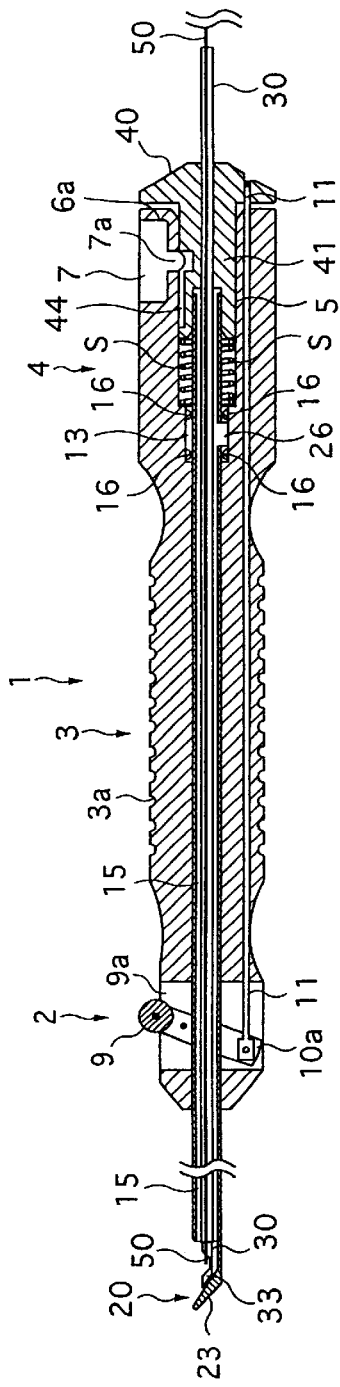

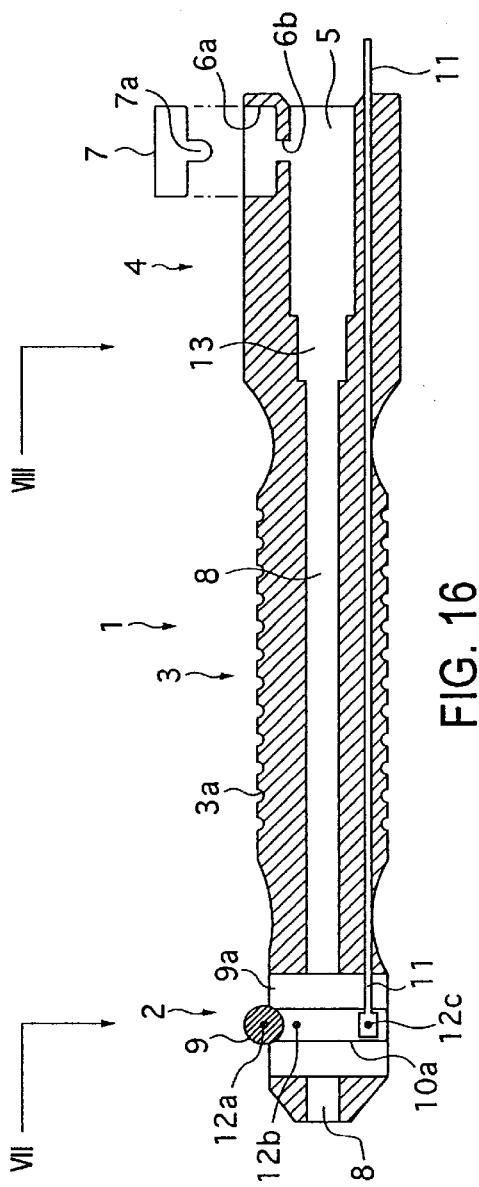
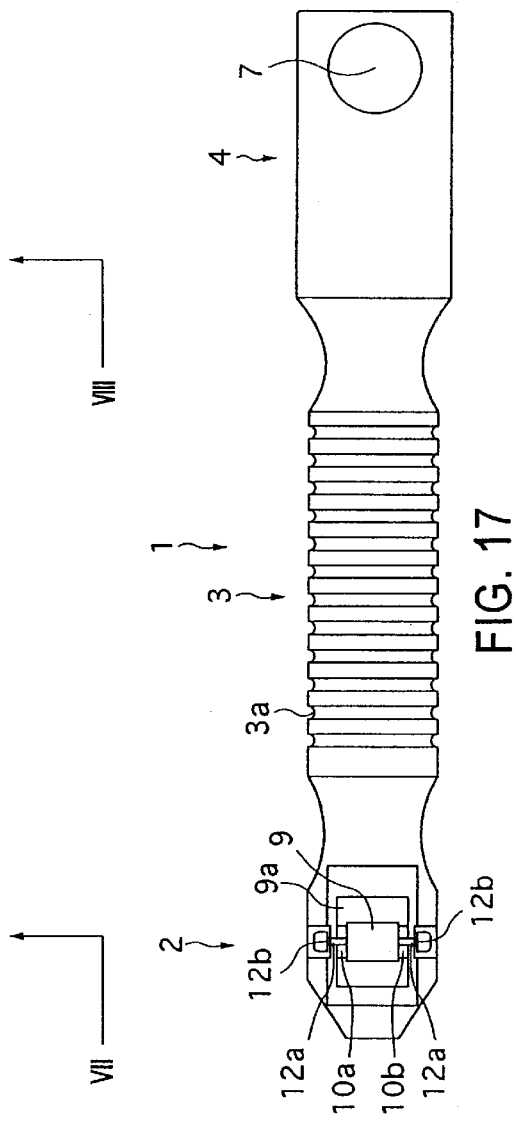
FIG. 16
FIG. 17

APPARATUS FOR MEDICAL TREATMENT

FIELD OF THE INVENTION

The present invention relates to an apparatus for medical treatment and in particular to an apparatus for medical treatment which is miniaturized to such a size that it can be used together with an endoscope and is capable of incising the living tissue with less bleeding.

BACKGROUND OF THE INVENTION

Recently, incision of the living tissue using laser light and the like has been commonly conducted since it is excellent in hemostasis. If the laser light is used, emission of the laser light from the front end of an optical fiber is concentionally conducted while the front end of the optical fiber is separated from a target tissue. However, by the reason of high damages to the apparatus components, irradiation of the living tissue with the laser light emitted from the surface of a probe has recently been conducted while the probe is in contact with the living tissue after the laser light has transmitted through the optical fiber to the emission probe and been incident upon the emission probe disposed in front of the front end of the optical fiber.

The present inventor has developed various contact type probes and they have been widely used. In order to incise the tissue by using such a contact type probe, it is necessary to cause the probe to track an incision line on the surface of the tissue on one side thereof a plurality of times. When a fine blood vessel is cut, bleeding is less since the blood vessel where it is irradiated with the laser light will be solidified. However, when a blood vessel having a diameter of 1.5 mm or more is to be cut, it is usually necessary to preliminarily knot the blood vessel on both sides of the cut position with a suture to prevent bleeding.

As far as one light guide probe is used in such a manner, it is necessary to knot a large blood vessel on the both sides of the cutting position every time when the blood vessel is cut. This will hinder the ready and easy operation. Although a suture which is biocompatible to the living tissue in recovery after operation has been developed, it is necessary to remove the suture from the tissue after opening the body again if the concrescence between the suture and the living tissue is not complete. This removing operation is hard on the patient.

If an organ which is easy to bleed such as liver is to be cut it is necessary to gradually cut the organ along the same incision line many times in order to minimize bleeding. It takes a long time to conduct the operation, and attention should be paid.

In case in which one of an organ has been already incised and the other has not been incised yet, even if irradiation with laser light is conducted plural times when some organ is to be cut or incised, the tissue behind the tissue to be treated is inevitably slightly irradiated with laser light by accident. On the other hand, in case of the projecting tumor, it has been known that the tumor is cut from the neck thereof with an annular radio frequency snare which is disposed around the tumor. This operation is not excellent in hemostasis. If physiological saline is used, an electric shock is given to the tissue and burn may occur in the vicinity of the diseased portion so that the tissue is unwatedly damaged.

From this point of view, in order to conduct at proper and quick surgical operation, cutting and incision of the tissue should be conducted one time operation, the hemostasis should be high and only target tissue should be able to be cut or incised and incision is possible without knotting if the target tissue is a blood vessel.

Therefore, the present inventor has proposed an apparatus for treatment which has overcome these problems in Japanese Unexamined patent publication No. Hei 3-218742. The apparatus for treatment using the laser light irradiation has two light guide probes which faces each other. The laser light emitting portions of the two light guide probes can be in and out of contact with each other by the surgical operators actuation. The laser light is incident to respective light guide probes via respective laser light transmitting systems. A target tissue to be treated is disposed between the laser light emitting portions of the light guide probes.

However, since the two light guide probes are linked to each other at their base ends so that they are substantially V-shaped and the target tissue is to be tweezed with a tweezers in prior art, the width of the apparatus per se and the range of actuation of the apparatus can not be made small. The prior art apparatus is suitable for the treatment in an open position in laparotomy, but is not suitable for the application in which the apparatus is inserted into a body cavity together with an endoscope.

In the above-mentioned prior art, it is necessary to pay attention so that the light guide probe will not be contact with the tissue in the vicinity of a target position to be treated even after the incision is completed since the light guide probe per se generates heat on incision.

Although the laser light is mainly directed toward the target position to be treated, some of the laser light is slightly incident upon the tissue other than the tissue to be treated. Accordingly, there is the risk in which the tissue in the vicinity of the target position to be treated will be damaged.

Although the prior art is capable of conducting incision and bleeding stopping simultaneously, the prior art is not ideal since the temperatures optimal for the incision and solidification of the living tissue are different.

SUMMARY OF THE INVENTION

It is a main object of the present invention to ideally conduct incision and bleeding stopping by one time operation, to miniaturize the apparatus for treatment to such a size that it can be inserted into a body cavity as well as an opening position together with an endoscope and to substantially prevent a damage to the living tissue other than a target position to be treated.

In order to accomplish the above-mentioned object, the present invention provides an apparatus for medical treatment characterized in that said apparatus comprises:

an outer probe which is in form of hook;

an inner probe which faces said outer probe and is capable of being in and out of contact with said inner probe in a longitudinal direction by the operator's actuation; and heating means for heating a target tissue to be treated which is disposed between said outer and inner probes.

Since the outer and inner two probes are brought into in and out of contact with each other by the operator's actuation in accordance with the present invention, treatment can be conducted without enlarging and opening the apparatus in a lateral direction. The apparatus can be miniaturized to such a size that it can be used together with an endoscope. Since incision of the target tissue to be treated is conducted by heating means for hiating the target tissue in interest while it is sandwiched between the hooked portions of two probes, incision and arresting of bleeding of the tissue can be achieved by one time operation.

Said heating means may be adapted to irradiate at least the inner probe of said outer and inner probe with laser light to cause said probe to generate heat.

Said heating means may be resistive heating means which is provided on one of said two probes.

Said heating means may comprise means for supplying said two probes serving as electrodes with a radio frequency current.

Said heating means may comprise means for causing one of said two probes to oscillate at ultrasonic frequency.

Said heating means may comprise for causing one of said two probe to serve as an antenna for emitting microwaves and in which the hook portion of said one probe is formed with a blade.

The surface of said outer or inner probe which faces a target tissue to be treated may have a function of cutting blade.

The present invention further provides an apparatus for medical treatment comprising;

an outer and inner hook probe, each comprising a hollow tubular member having a portion in the form of hook at the front end thereof;

said inner hook probe being inserted into said outer hook probe;

the front end portion of said inner hook probe being capable of being brought in or out of contact with the hook portion of said outer hook probe by the actuation of a surgical operator; and heating means for heating a target tissue to be treated while said target tissue to be treated is sandwiched between at least the hooked portion of said outer hook probe and the front end portion of the inner hook probe.

Said inner hook probe may be made of a hollow tubular member having a hooked portion at the center thereof, said heating means comprising a heater element provided on the hooked portion of said inner hook probe, which absorbs the laser light to generate heat and laser light transmitting and irradiating means which is inserted into said inner hook probe for irradiating said heater element with laser light.

Said heating means may be resistive heating means which is provided on one of said two probes.

Said heating means may comprise means for supplying said two probes serving as electrodes with a radio frequency current.

Said heating means may comprise means for causing one of said two probes to oscillate at an ultrasonic frequency.

Said heating means may comprise for causing one of said two probe to serve as an antenna for emitting microwaves and in which the hook portion of said one probe is formed with a blade.

The surface of said outer or inner probe which faces a target tissue to be treated may have a function of cutting blade.

The present invention further provides an apparatus for medical treatment comprising an outer probe which is made of a hollow tubular member having a chisel blade like front end which is integrally formed so that it is extended from a part of the outer periphery at the front end in a longitudinal direction; and an inner probe which is inserted into said outer probe and is extendable from said chisel blade like front end of the outer probe by the actuation of a surgical operator;

said inner probe including heating means for heating a target tissue to be treated.

Said outer probe may be formed in such a manner that said chisel blade like front end is bent toward the axis of said outer probe and the bent chisel blade like front end is provided with a notch extending from said front end thereof.

Said inner probe may be a laser probe which faces the target tissue to be treated for irradiating it with laser light.

Said inner probe having a laser probe may comprise a probe which is in the form of trowel at the front end thereof and laser like transmitting and irradiating means for irradiating at least the front end portion of said probe with laser light.

BRIEF DESCRIPTION OF THE DRAWINGS

FIG. 1 is a longitudinal sectional view showing an apparatus for medical treatment of a first embodiment of the present invention;

FIG. 2 is a view showing the operation of the apparatus in FIG. 1;

FIG. 16 is a longitudinal sectional view showing a handpiece;

FIG. 17 is a upper face view showing the handpiece in FIG. 16;

DESCRIPTION OF THE PREFERRED EMBODIMENT OF THE PRESENT INVENTION

Now, the present invention will be described in detail by way of embodiments by reference to the drawings.

FIG. 1 shows a first embodiment of an apparatus for medical treatment of the present invention. The apparatus mainly comprises an outer hook prove 20, inner hook prove 30, handpiece 1 which serves as means for bringing the prove 20 in and out of contact with the prove 30 by an operator's operation and laser light transmitting irradiating means 50 which serves as heating means for heating a target to be treated.

Figure 3:
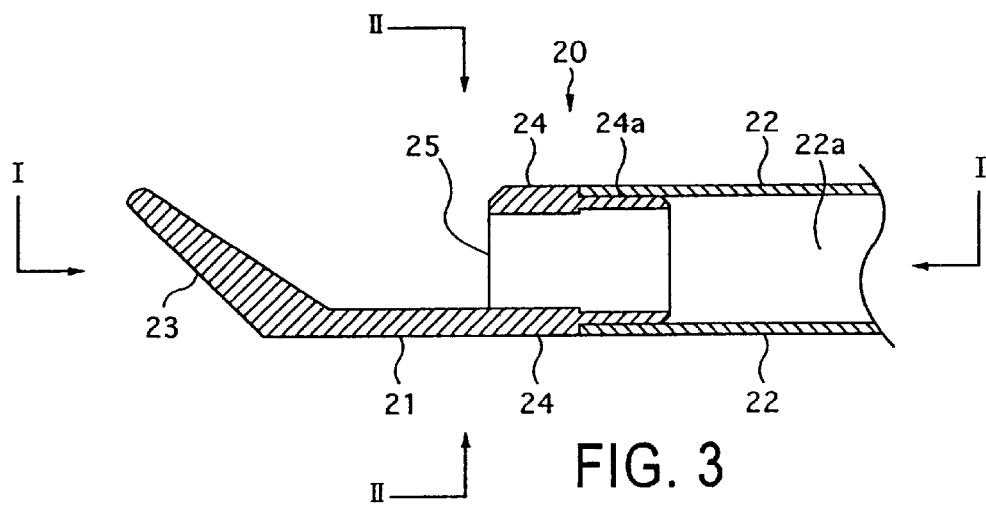
FIG. 3 is a longitudinal sectional view of an outer hook prove in a first embodiment of the present invention.
Figure 4:
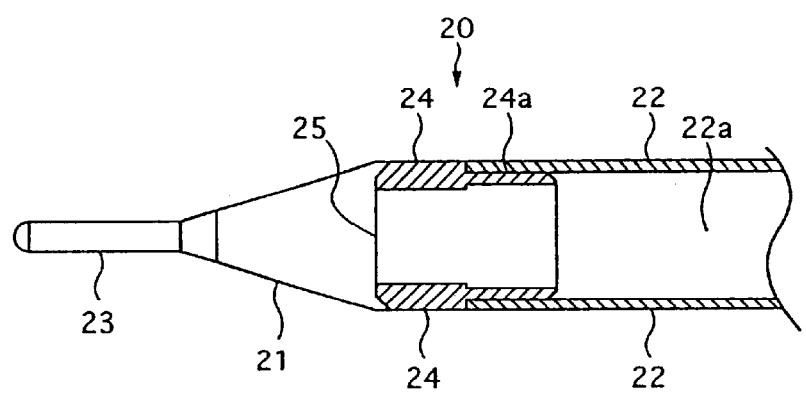
FIG. 4 is a sectional view taken along the line I—I in FIG. 3.
Figure 5:
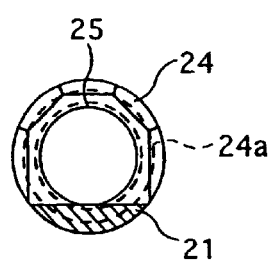
FIG. 5 is a sectional view taken along the line II—II in FIG. 3.

Now, the outer hook prove 20 (hereinafter referred to as outer hook) in the first embodiment will be described in detail. As shown in FIGS. 3 to 5, the outer hook 20 comprises a hollow tubular member 22 and a hook member 21 in the form of hook at the front end thereof, which is integrally provided on the front end of the hollow tubular member 22. In the first embodiment, the hook member 21 is formed at the base end portion 24 on its outer periphery thereof with a step portion 24a. The hollow tubular member 24 is linked to hook member 21 by fitting the step portion 24a into the hollow tubular member 22. It is of course that the hollow tubular member 22 of the outer hook 20 and the hook member 21 may be initially formed as an integral member.

The hook member 21 of the outer hook 20 has the base end portion 24 and a hook portion 23. The base end portion 24 is tubular in shape. The hook portion 23 extends from a part of the outer periphery of the base end portion 24 at the front end side thereof in a tapered manner and is bent at the front end thereof. The base end portion 24 of the hook member 21 forms an opening 25 facing the inner side of the hook portion 23 by substantially extending a hollow passage 22a within the hollow tubular member 22 while the hook member 21 is linked to the hollow tubular member 22.

Since it is a main object of the hook portico 23 of the outer hook 20 to hold a target to be treated by hooking it as will be described below, It may have an appropriate shape as far as the object can be achieved or depending upon the position of the target to be treated. It is preferable that the hook member 23 be formed so that it is rounded at the front end thereof.

Figure 6:
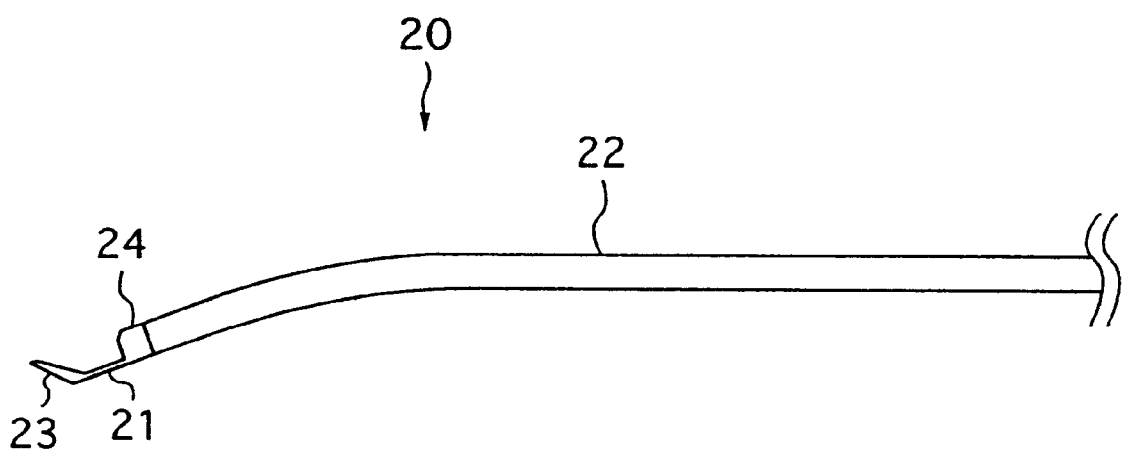
FIG. 6 is a front view showing another form of the outer hook prove.

The hollow tubular member 22 of the outer hook 20 may be formed so that it is straight in a longitudinal direction. Alternatively, it may be curved depending upon the position of the target to be treated as shown in FIG. 6.

The outer hook 20, at least the outer periphery of the hook member 23 is provided with heat resistance and heat insulation. Specifically, the hook member 23 is formed of a material having a rigidity such as stainless steel and is plated with gold and then coated with a heat resistance fluorine resin thereon. This prevents the heat from the inner hook 30 which will be described below from conducting to the outer periphery of the outer hook. Even if the outer surface of outer hook 20 is brought into contact with the living tissue, no burn of the tissue in interest occurs. Heat resistant epoxy resin or ceramics may be used in lieu of the heat resistant fluorine resin. The outer hook may be directly coated with ceramics such as $ZrO_2$. The hollow tubular member of the outer hook may preferably be made of stainless steel tube.

The outer hook 20 preferably has an outer diameter of about 5 mm or less depending upon the position of the target to be treated. Although the length of the outer hook 20 may be appropriately selected depending upon the position of the target to be treated or the surgical method, the operatability of the apparatus is excellent so that precision surgical operation can be achieved when the length of the outer hook 20 from the front end face of the handpiece is about 40 to 400 mm while it is mounted on a hand piece 1 which will be described below.

Figure 7:
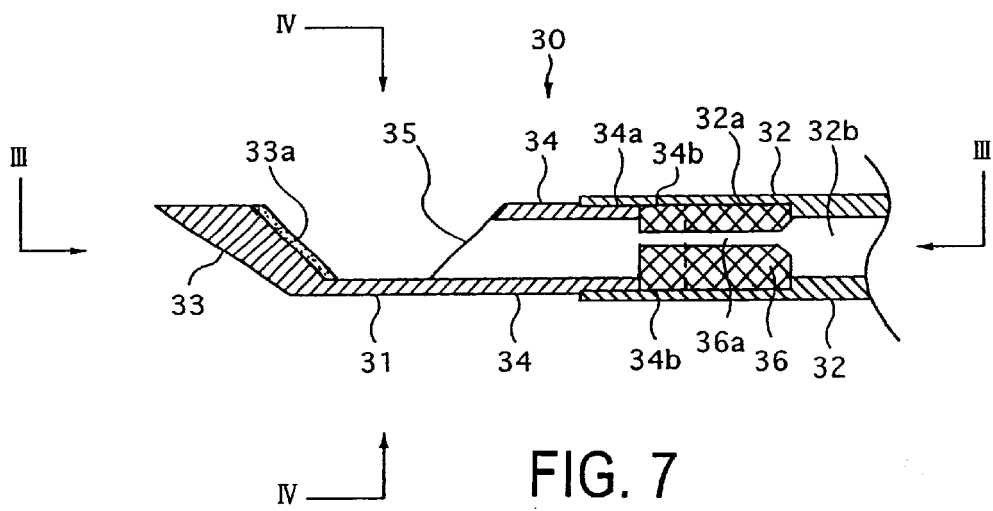
FIG. 7 is a longitudinal sectional view showing an inner hook prove in the first embodiment of the present invention.
Figure 8:
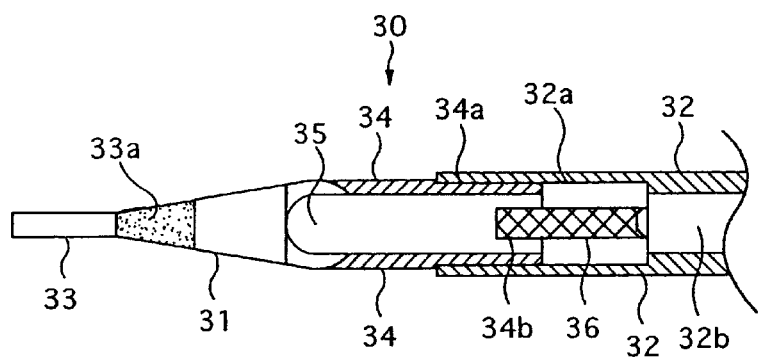
FIG. 8 is a sectional view taken along the line III—III in FIG. 7.
Figure 9:
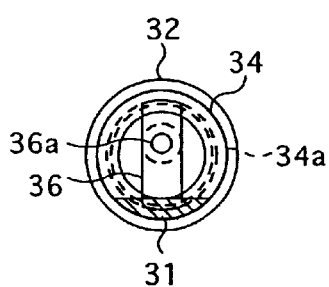
FIG. 9 is a sectional view taken along the line IV—IV in FIG. 7.

FIGS. 7 to 9 shows the inner hook probe (herein after referred to as inner hook) 30 in the first embodiment. The inner hook has a shape which is substantially similar to that of the above mentioned outer hook 20. In other words, the inner hook 30 comprises a hollow tubular member 32 and a hook member 31 which integrally extends from the front end of the hollow tubular member 32. The hook member 31 is in the form of hook at the front end thereof. The hook member 31 is formed at the base end portion 34 on the outer periphery thereof with a step portion 34a. The step portion 34a is fitted to a step portion 32a which is provided on the front end side of the hollow tubular member 32 so that the hollow tubular member 32 is linked to the hook member 31. The hook member 31 of the inner hook 30 has the base end portion 34 and a hook portion 33. The base end portion 34 is tubular in shape and is cut at an angle of about 45 degrees at the front end thereof. The hook portion 33 extends from a part of the periphery of the base end portico 34 on the front end side thereof and is bent at the front end thereof. The base end portion 34 of the hook member 31 substantially extends a hollow passage 32b within the hollow tubular member 32 to constitute an opening 35 facing the inner side of the hook portion 33 while the hook member 31 is linked to the hollow tubular member 32.

The inner hook 30 in the first embodiment is provided with notches 34b which face the outer periphery of the step portion 34a of the hook member 31. The inner hook 30 comprises a laser light transmitting and irradiating means holding member 36 which is adapted to the notches 34b and the step portion 32a which is provided on the front end side of the hollow tubular member 32. The laser light transmitting and irradiating means holding member 36 constitutes a passage 36a for holding the laser light transmitting irradiating means.

Since the inner hook 30 is inserted into the outer hook 20 in such a manner that a given gap is preferably formed therebetween, the inner hook 30 has an appropriate size and shape so far as the gap is formed. The inner hook 30 has preferably a diameter of 2 to 3 mm. As shown in FIGS. 10 and 11, the hook portion 33 of the inner hook 30 has such an appropriate shape that the outer surface of the hook portion 33 of the inner hook 30 abuts to, preferably tightly fits to the inner surface of the hook portion 23 of the outer hook 20 within an insertion limit of the inner hook 30 into the outer hook 20.

The inner hook 30 is provided with a heating element which is heated by absorbing the laser light. Preferably, the hook member 33 is made of a material which is excellent in heat conductivity. The hook portion 33 is provided on the inner surface thereof with a heating element 33a which absorbs the laser light to generate heat. Specifically, the hook member 33 of the inner hook 30 is made of a material having a rigidity such as stainless steel. The hook portion 33 is formed on the inner surface thereof with the heating element 33a which is made of a material which absorbs the laser light to generate heat, such as carbon, graphite, iron oxide, manganese oxide.

The heating element 33a maybe formed by coating the inner surface of the hook portion with a coating composition which is a mixture of powder of carbon, graphite, iron oxide, manganese oxide with a heat resistant binder such as artificial or natural sapphire, quartz, glass, heat resistant plastics.

Figure 12:
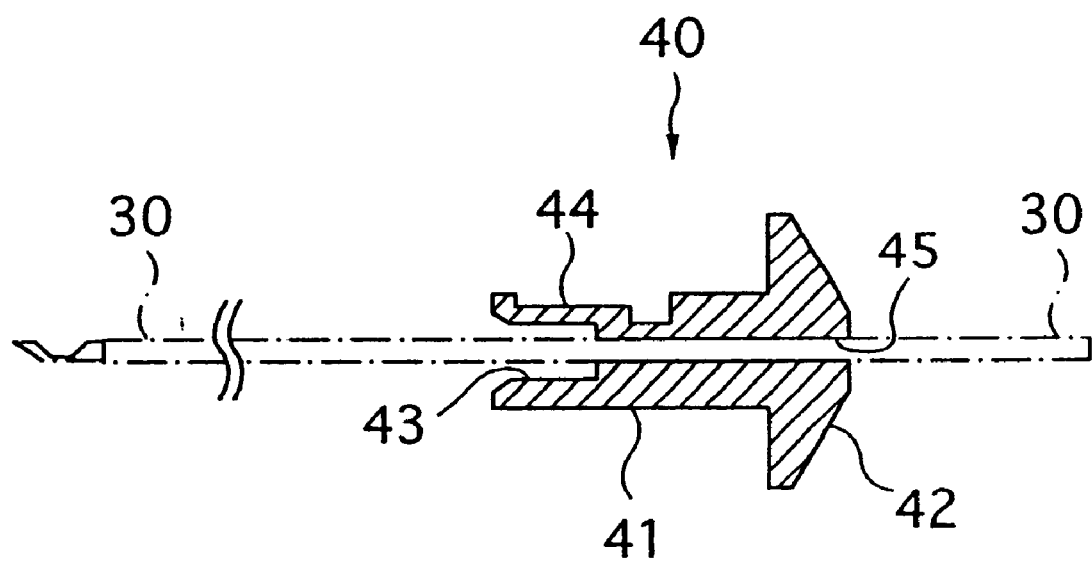
FIG. 12 is a longitudinal sectional view showing the inner hook holder.

FIG. 12 shows an inner hook holder 40. The inner hook holder 40 has a shank 41 and head 42. The shank 41 is formed with a concave hole 43 which extends toward the head 42 along the axis thereof from one end of the shank 41 to a substantially intermediate point thereof. The inner hook holder 40 is formed with a guide groove 44 which extends along the axis thereof from a substantial center of the outer periphery of the head 41 to a position before the end of the shank 41. The inner hook holder 40 is also formed with a passage 45 extending from the end of the head 42 along the axis thereof to communicate with the concave hole 43 in the shank 41. The above-mentioned inner hook 30 is inserted into the passage 45 for passing through the inner hook holder 40.

Figure 13:
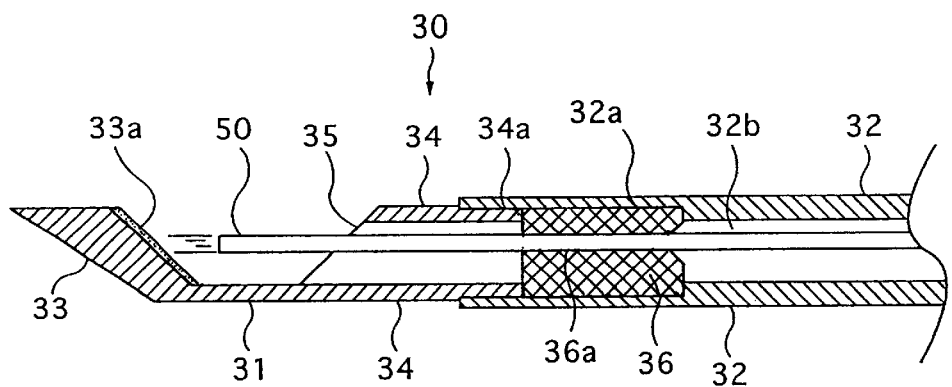
FIG. 13 is a longitudinal sectional view showing the inner hook prove in which laser light transmitting and irradiating means is disposed.

On the other hand, laser light transmitting and irradiating means 50 is inserted into the inner hook 30 as shown in FIG. 13. Specific example of the laser light transmitting and irradiating means 50 may include an optical fiber and the like. The laser light transmitting and irradiating means 50 is coupled to a laser light generator (not shown) for supplying the laser light thereto. The optical fibers having an outer diameter of 300 to 1000 μm may be preferably used. The laser light from the laser light generator may includes argon laser light or diode laser light although Nd-YAG laser light is optimal. The laser light transmitting and irradiating means 50 is inserted into the passage 36a of the above-mentioned laser light transmitting and irradiating means holding member 36 from the rear end of the inner hook 30 and is held therein and extends beyond the opening 35 of the hook member 31 of the inner hook 30 to face the heating portion 33a on the inner surface of the hook portion 33.

Figure 14:
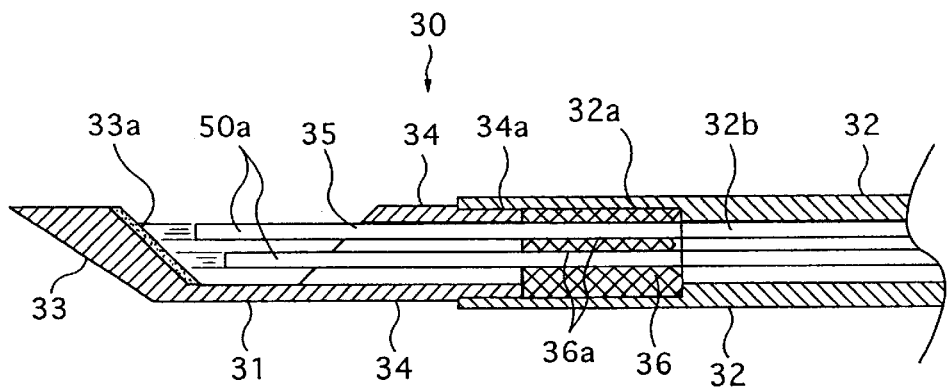
FIG. 14 is a longitudinal sectional view showing the inner hook prove in which another form of laser light transmitting and irradiating means is disposed.
Figure 15:
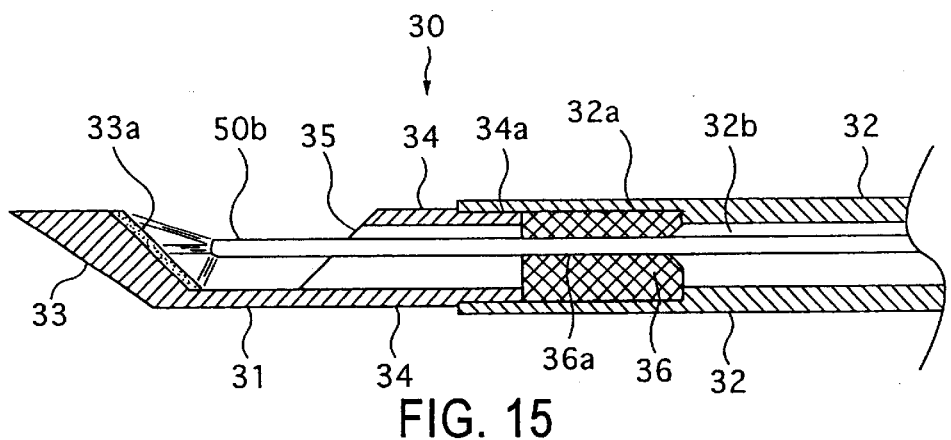
FIG. 15 is a longitudinal sectional view showing the inner hook prove in which a further form of laser light transmitting and irradiating means is disposed.

Alternatively, it is preferable to use two optical fibers 50a serving as laser light transmitting and irradiating means, which extend in a longitudinal direction in a parallel relationship to each other as shown in FIG. 14. Further alternatively, three beams of laser light can be emitted by cutting the optical fiber 50b at the front end face thereof to provide three end faces as shown in FIG. 15 even when only one optical fiber is used. It is preferable to cut the optical fiber at the front end face thereof to provide two end faces.

FIG. 16 is a longitudinal sectional view showing a handpiece 1 and FIG. 17 is an upper face view showing the handpiece in FIG. 16. The handpiece 1 is substantially cylindrical in shape and is formed in a substantially intermediate position along the length thereof with a grip portion 3. The grip portion 3 is provided on the outer periphery thereof with a plurality of circumferential grooves 3a to provide non-slip properties.

Figure 18:
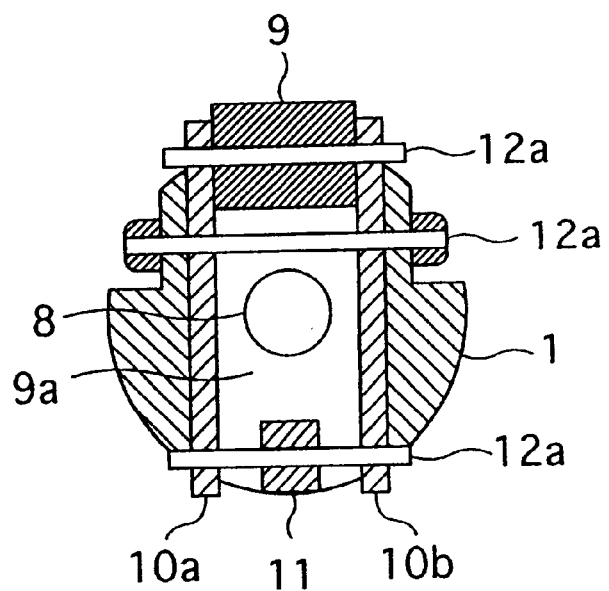
FIG. 18 is a sectional view taken along the line VII—VII in FIG. 16.

The handpiece 1 is formed at the rear end portion 4 thereof with a concave hole 5 extending along the axis thereof from the rear end face of the handpiece 1 into which the inner hook holder is inserted. The handpiece 1 is formed on the outer periphery of the rear end portion 4 with a recess 6a for the inner hook holder retaining switch 7. The recess 6a and the recess hole 5 at the rear end of the handpiece are in communication with a communication hole 6b. The inner hook holder retaining switch 7 having a convex 7a projecting into the concave hole 5 at the rear end of the handpiece through the communication hole 6b is disposed within the recess 6a. It is preferable that the inner hook holder retaining switch 7 be provided on the outer periphery of the handpiece on the side opposite to feeding and discharging passages 15a and 15b (refer to FIG. 18) which will be described below.

The handpiece 1 is formed with a passage 8 extending along the axis thereof from the front end face so that the passage 8 is in communication with the concave hole 5 at the rear end portion 4 via a feeding and discharging chamber 13. Since the hollow tubular member 22 of the above-mentioned outer hook 20 is inserted and secured to the passage 8, the passage has an appropriate inner diameter corresponding to the outer diameter of the hollow tubular member 22.

Figure 19:
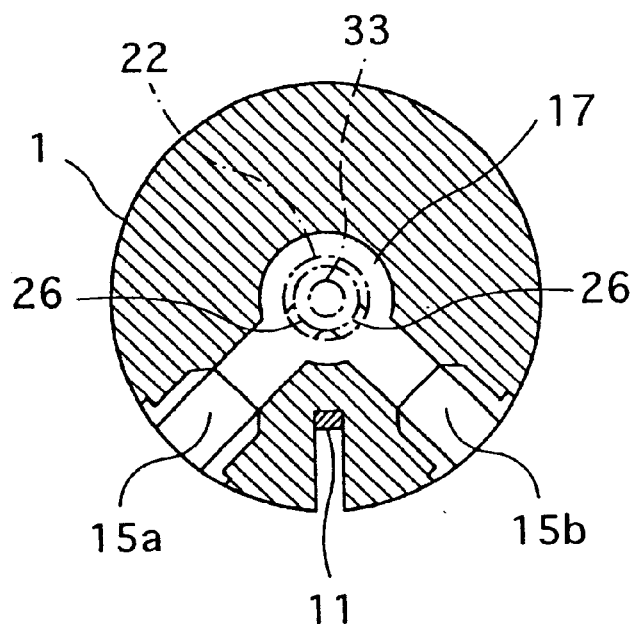
FIG. 19 is a sectional view taken along the line VIII—VIII in FIG. 16.

The front end portion 2 of the handpiece 1 is formed with a hole 9 extending therethrough from one side of the outer periphery thereof to the other side thereof. As is particularly clear from FIG. 18, a substantially cylindrical inner hook actuating switch 9 is provided in the hole 9a as shown in the upper side in FIG. 18 so that it is journalled by a pin 12a which extend through the axis of the switch 9. The switch 9 is linked to one end of link members 10a and 10b which face each other with respect to the hole 8. The link members 10a, 10b are rotatably supported by the pin within the hole 9a on the side of the actuating switch 9 with respect to its gravity. While the link members 10a, 10b are linked to a reciprocal member 11 on the other side thereof by the pin 12c. The reciprocal member 11 is disposed in a groove extending in a longitudinal direction of the handpiece 1 to the rear end face thereof below the passage 8 so that it extends from the rear end face of the handpiece. Accordingly, the reciprocal member 11 is reciprocated via the link members 10a, 10b in association with the reciprocal movement of the inner hook actuating switch 9 in a longitudinal direction. As also shown in FIG. 19, the feeding and discharging passage constituting chamber 13 in the rear end portion 4 of the handpiece is provided with feeding and discharging passages 15a, 15b extending from the outer periphery of the handpiece, which are in communication therewith. The feeding and discharging passages 15a and 15b are provided so that they overhang the reciprocal member 11 in a radial direction of the handpiece 1. Although the feeding and discharging passages 15a, 15b are provided on the side opposite to the actuating switch 9 so that they extend toward the outer periphery of the rear end portion 4, they may be provided on the same side as the actuating switch 9.

These parts are arranged as shown in FIG. 1. In other words, the outer hook 20 is inserted and secured to the passage 8 of the handpiece 1 so that its rear end portion extends to an appropriate position in the concave hole 5 in the rear end portion of the handpiece 1.

The inner hook 30 is inserted into the inner hook holder 40 while it holds the inner hook 40 at the base end of the outer hook 20 within the concave hole 5 formed at the rear end of the handpiece 1. In an assembled condition, the concave 7a of the inner hook holder retaining switch 7 of the handpiece 1 is engaged in the guide groove 44 of the shank of the inner hook holder 40. As a result of this, the inner hook holder 40 is movable in a longitudinal direction thereof in a range where the guide groove 44 is formed.

Figure 10A:
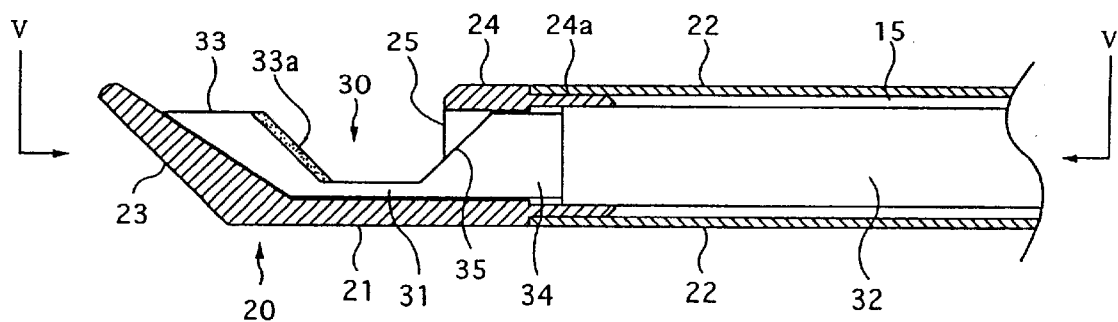
FIG. 10(a) is an enlarged longitudinal sectional view of main parts showing the condition in that the inner hook prove is disposed within the outer hook prove.
Figure 10B:
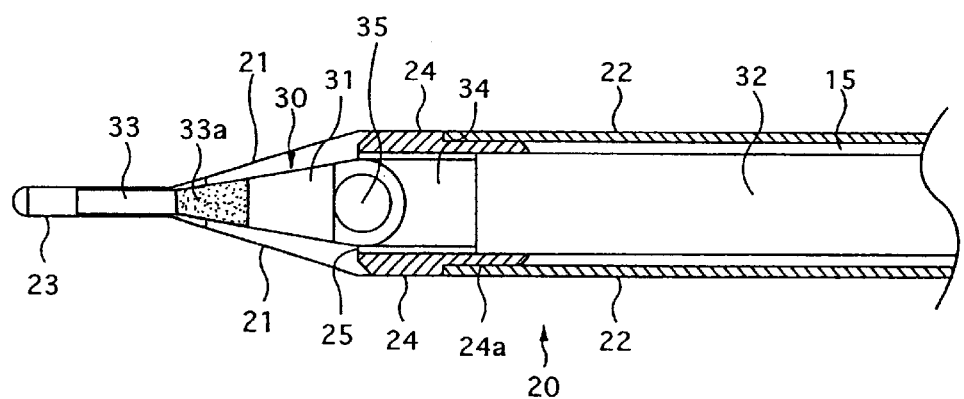
FIG. 10(b) is a sectional view taken along the line V—V in FIG. 10(a)
Figure 11A:
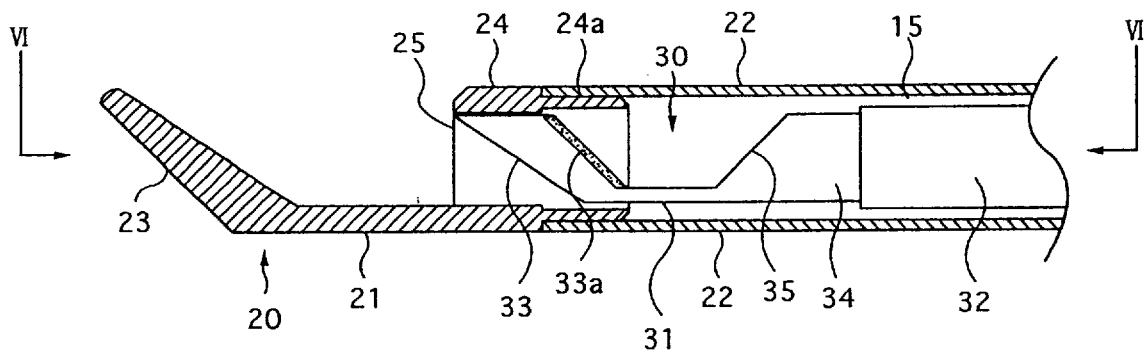
FIG. 11(a) is an enlarged longitudinal sectional view of main parts showing another condition in that the inner hook prove is disposed within the outer hook prove.
Figure 11B:
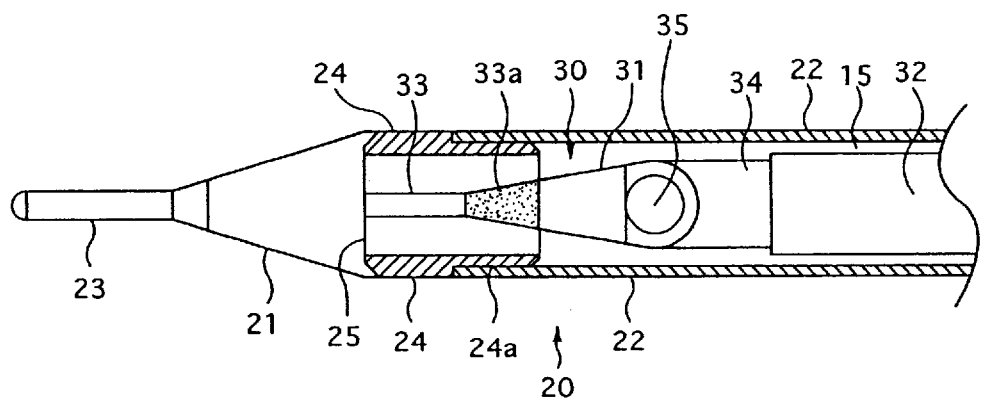
FIG. 11(b) is a sectional view taken along the line VI—VI in FIG. 10(a)

In the assembled condition, the inner hook holder 40 is secured to the reciprocal member 11 projecting from the rear end face of the handpiece 1. Accordingly, reciprocal movement of the actuating switch 9 allows the inner hooke 30 to reciprocate in a longitudinal direction via the link members 10a, 10b, reciprocal members 11 and inner hook holder 40. The range of reciprocal movement of the inner hook 30 is set from a position in which the outer face of the hook portion 33 abuts to the inner surface of the hook portion 23 of the outer hook 20 as shown in FIGS. 1, 10(a) and 10(b) to a position in which at least the front end of the inner hook 30 is concealed within the base end portion 24 of the hook member 21 of the outer hook 20 as shown in FIGS. 2, 11(a) and 11(b). The range of reciprocal movement of the inner hook 30 is set by the fact that the range of the reciprocal movement of the link members 10a, 10b is limited by the inner wall of the hole 9a in the front end portion 2 of the handpiece 1. The range of reciprocal movement of the inner hook 30 may be set by the length of the guide groove 44 of the shank 41 of the inner hook holder 40 in a longitudinal direction thereof.

In the first embodiment, a spring S is disposed between the end face of the inner hook holder 40 and the inner end face of the concave hole 5 in the handpiece 1 so that the inner hook holder 40 is biased in a rear direction thereof. Accordingly, the front end of the inner hook 30, that is the front end of the hook portion 33 is normally concealed within the base end portion 24 of the hook member 21 of the outer hook 20 as shown in FIG. 1. On the other hand, in order to remove the inner hook holder 40, the inner hook holder 40 is drawn from the handpiece 1 by pulling up the inner hook holder retaining switch 7.

Before or after insertion of the inner hook 30 and inner hook holder 40 into the handpiece 1, the laser light transmitting and irradiating means 50 is inserted into the inner hook 30 so that the front end of the inner hook 30 faces the inner face of the hook portion 33 of the inner hook 30 and is separated therefrom at an appropriate distance.

In the assembled condition, a gap 15 is formed between the inner surface of the hollow tubular member 22 of the outer hook 20 and the outer surface of the hollow tubular member 32 of the inner hook 30. The outer hook 20 is preliminarily provided with a communication port 26 in a position where the feeding and discharging passage constituting chamber 13. Seal rings 16 are disposed within the feeding and discharging passage constituting chamber 13 in front of or in the rear of the communication port 26 in a longitudinal direction so that a tubular passage 17 (refer to FIG. 19). The gap 15 between the inner surface of the hollow passage 22a of the outer hook 20 and the outer surface of the hollow passage 32b of the inner hook 30 is communicated with the feeding and discharging passages 15a, 15b of the handpiece 1 through the tubular passage 17.

The manner of actuation and operation of the first embodiment of the present invention which has been described will be described with reference to cutting of a blood vessel.

Figure 20:
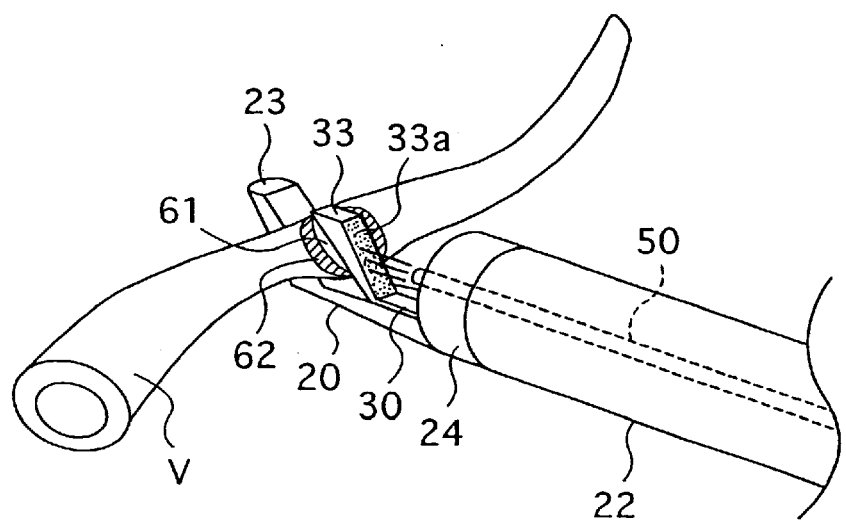
FIG. 20 is an explanatory view illustrating the condition in which cutting of a blood vessel is conducted by means of the apparatus of the first embodiment of the present invention.
Figure 21:
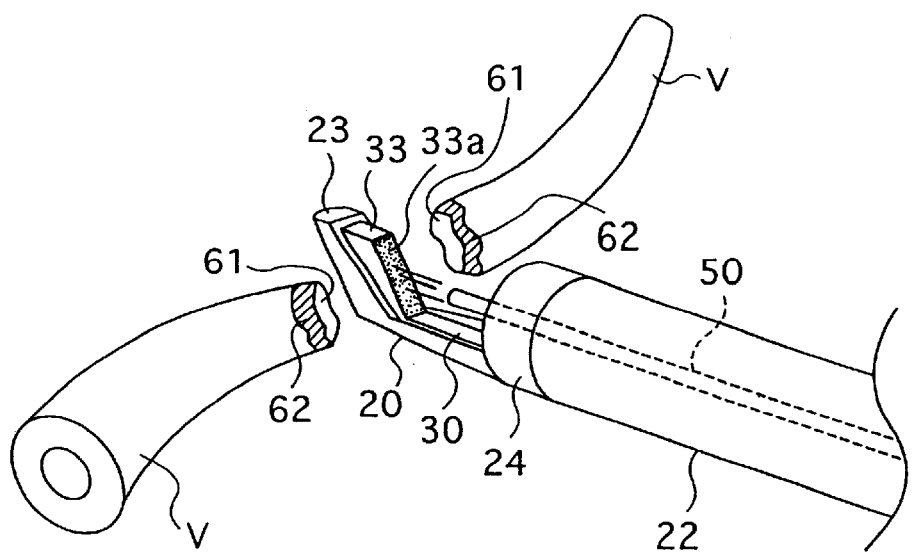
FIG. 21 is an explanatory view illustrating the condition after cutting of the blood vessel has been conducted by means of the apparatus of the first embodiment of the present invention.

FIGS. 20 and 21 are explanatory views showing that a blood vessel is cut by means of the apparatus for medical treatment of the first embodiment. As shown in FIG. 20, the blood vessel V to be cut is disposed between the inner surface of the hook portion 23 of the outer hook 20 and the outer surface of the hook portion 33 of the inner hook 30. This operation is achieved by actuating the actuating switch 9 at the front end of the handpiece 1 (by pulling the switch in a rearward direction as shown in FIG. 2). Subsequently, the inner surface of the hook portion 33 of the inner hook 30 is irradiated with laser light which is generated by a laser light generator (not shown) from the front end of the laser light transmitting and irradiating means 50 while pulling the actuating switch 9. The heating portion 33a formed on the inner surface of the hook portion 33 is heated. In association with this, the outer surface of the hook portion 33 of the inner hook 30 is heated. Heating of the outer surface of the hook portion 33 of the inner hook 30 causes the blood vessel V between the inner surface of the hook portion 23 of the outer hook 20 and outer surface of the hook portion 33 of the inner hook 30 to be vaporized and cut.

Although not shown in FIGS. 20 and 21, it is preferable to conduct suction and discharge of supplied washing water, vaporized fume or material or blood by means of pumping means (not shown) via feeding and discharging passages 15a, 15b which are formed by the gap 15 and the tubular passage 17 between the outer hook 20 and the inner hook 30 during and after the incision.

Although the inner surface of the hook portion 33 of the inner hook 30 is mainly irradiated with the laser light in the first embodiment, the blood vessel tissue 61 in the vicinity of the inner surface of the hook portion 33 is also irradiated with the laser light. As a result, the adjacent blood vessel tissue 62 is heated to a relatively low temperature to solidify the blood vessel tissue in the vicinity of the vaporized and cut portion. Accordingly, each of the blood vessels which have been cut will comprise a completely sealed portion having a vaporized portion 61 and solidified portion 62 as shown in FIG. 21.

In such a manner, the energy of the laser light for the irradiation is distributed to those for vaporization and solidification in the apparatus for medical treatment of the first embodiment of the present invention. The proportion of the distribution of the energy of the laser light can be adjusted by changing the distance between the front end of the laser light transmitting and irradiating means 50 and the inner surface of the hook portion 33 of the inner hook 30. The vaporization effect will become stronger as the distance decreases. The solidification effect will become stronger as the distance increases. Specifically, it is preferable to change the ratio of the laser light for the irradiation in such a manner that the outer surface of the hook portion 22 of the outer hook 20 is irradiated with the 80 to 10% of the laser light and the inner surface of the hook portion 33 of the inner hook 30 is irradiated with 20 to 90% of the laser light when the laser light is incident to the inner surface of the hook portion 33 of the inner hook 30 while nothing is disposed between the inner surface of the hook portion 23 of the outer hook 20 and the outer surface of the hook portion 33 of the inner hook 30.

Since the hook portion 23 of the outer hook 20 is provided on at least the outer surface thereof with a heat insulation as mentioned above, heat of the inner hook 30 will not conduct to the outer surface of the outer hook 20. Even if the outer surface of the outer hook 20 will contact with the other tissue during and after incision, damages such as burn will not given to the tissue. Since the hook portion 33 of the inner hook 30 which is still heated can be housed into the outer hook 20 by releasing or moving the actuating switch 9 in a forward direction after cutting, The inner hook 30 will not contact with the other tissue when the apparatus is moved.

Although the inner hook prove and the laser light transmitting and irradiating means are used as means for heating a target to be treated in the above-mentioned first embodiment, an alternative heating means may be proposed. In accordance with a second embodiment, an apparatus for treatment in which a resistive heating element on the inner surface of the hook portion of the inner hook is provided in lieu of the heating element which generates heat on exposure to the laser light in the above-mentioned first embodiment. Accordingly, the laser light transmitting and irradiating means in the above-mentioned first embodiment is not essential in the second embodiment. In this case, ceramics resistor or nichrome resistor and the like may be preferably used as the resistive heating element in this case. The inner and outer hooks are coated with, for example, heat resistant fluorine resin so that they are completely insulated.

On treatment, a target tissue to be treated is sandwiched between the outer hook and the inner hook as is similar to the first embodiment, while the resistive heating element on the inner hook is heated. The resultant heating of the inner hook per se causes the tissue to be vaporized and be incised and the incised tissue in interest will be solidified. The ratio of the strength of the vaporization to that of the solidification can be adjusted by appropriately adjusting a voltage which is applied to the resistive heating element in the second embodiment.

Figure 22:
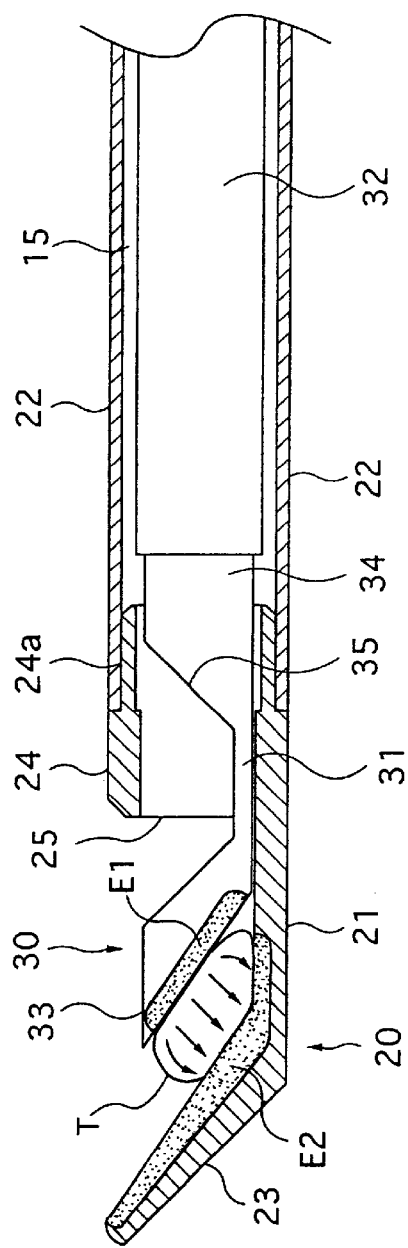
FIG. 22 is an enlarged longitudinal sectional view of main parts showing a third embodiment of the present invention.

FIG. 22 shows a third embodiment of the present invention. In the third embodiment, an electrically conductive electrode E1 is provided on the outer surface of the hook portion 33 of the inner hook 30 and an opposite electrode E2 is provided on the inner surface of the hook portion 23 of the outer hook 20 in position where the inner surface of the hook portion 23 of the outer hook 20 is abut to the outer surface of the hook portion 33 of the inner hook 30 in lieu of the heating element on the inner surface of the hook portion 33 of the inner hook 30 in the above-mentioned first embodiment. A radio frequency current is caused to flow across both electrodes while the target tissue to be treated is sandwiched therebetween. In this case, the outer hook 20 and the inner hook 30 is coated with, for example, heat resistant fluorine resin coat excepting the electric conducting electrode E1 and opposite electrode E2.

In the third embodiment, a radio frequency current is caused to flow across the electrode E1 and the opposite electrode E2 as shown by an arrow in the drawing while a tissue T to be treated is sandwitched between the electrodes E1 and E2 as shown in FIG. 22. The tissue T is heated so that the tissue is incised due to vaporization thereof and the cut portions of the tissue are solidified. In the third embodiment, the ratio of the strength of the vaporization to that of solidification can be adjusted by appropriately adjusting the frequency of the high frequency current.

A fourth embodiment of the present invention is proposed including an outer hook and inner hook which are similar to those in the above-mentioned first embodiment, in which means for causing the ultrasonic vibration of the inner hook is provided.

In this embodiment, the ultrasonic wave vibration of the inner hook is caused while a target tissue to be treated is sandwiched between the outer hook and the inner hook. Incision of the tissue is conducted by vaporization and the solidification of the tissue in cut position. The ratio of the strength of vaporization to that of solidification can be adjusted by appropriately adjusting the frequency of the ultrasonic wave.

In the above-mentioned first to fourth embodiments, a sharp blade may be formed on the outer surface of the hook portion of the inner hook which will abut to the inner surface of the hook portion of the outer hook. In this case, incision is conducted by means of the blade on the outer surface of the inner hook and the heating of the inner hook or the tissue is adjusted to a temperature which is optimal for the solidification thereof. Accordingly, the tissue in interest can be ideally solidified simultaneously with the incision of the living tissue.

Alternatively, a fifth embodiment of the apparatus for medical treatment of the present invention is proposed, including an outer hook and inner hook similarly to the above-mentioned first embodiment. The outer hook is formed of ceramics and the inner hook is made of a metal. A sharp blade is formed on the outer surface of the hook portion of the inner hook which will abut to the inner surface of the hook portion of the outer hook. The inner hook serves as an antenna for emitting microwaves.

In this embodiment, incision of the living tissue is conducted by the blade on the outer surface of the inner hook while the tissue to be treated is sandwiched between the outer hook and the inner hook. Simultaneously with this, solidification of the living tissue on the incision position is conducted by emitting the microwaves toward the incision position from the inner hook serving as an antenna. Although the heating element, laser light transmitting and irradiating means, and the laser light generator in the first embodiment are not essential in the above-mentioned second to fourth embodiments, they may be preferably used.

Figure 23:
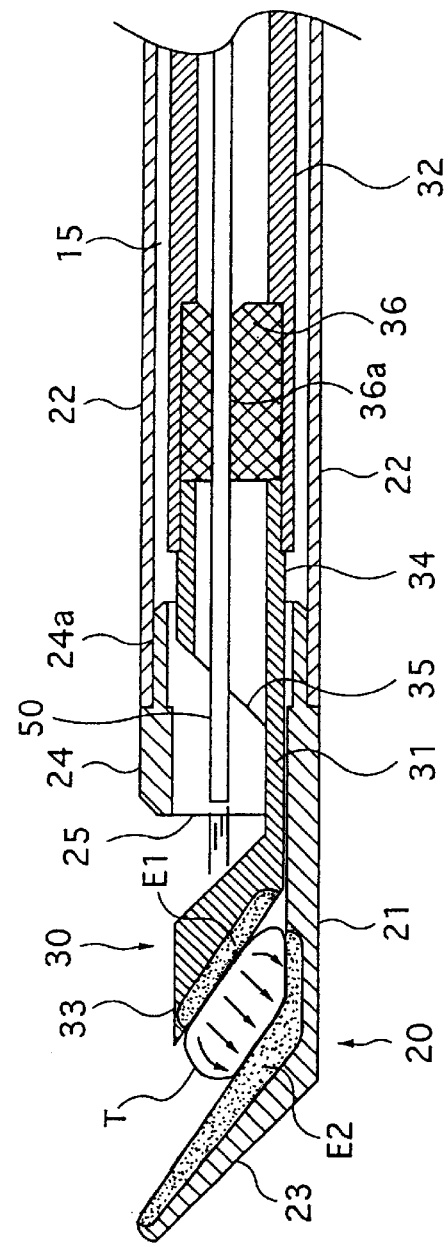
FIG. 23 is an enlarged longitudinal sectional view of main parts showing a sixth embodiment of the present invention.

For example, an apparatus for treatment (sixth embodiment) is proposed including the laser light transmitting and irradiating means 50 in the inner hook 30 in which incision of the tissue to be treated is conducted by the radio frequency current and solidification of the tissue in the vicinity of the incision position is conducted by the laser light emitted from the laser light transmitting and irradiating means 50 while the tissue to be treated is sandwiched between the inner surface of the hook portion 23 of the outer hook 30 and the outer surface of the hook portion 33 of the inner hook 30 as shown in FIG. 23. Although solidification of the living tissue by the radio frequency current will give a large damage thereto, both incision and solidification can be ideally achieved since the solidification of the tissue in the vicinity of incision position is conducted by the laser light.

The above-mentioned apparatus for medical treatment of the present invention is preferable in particular for cutting of the blood vessel and the like and is capable of ideally conducting incision and hemostasis by one operation. Since the front end of the prove is only moved in a longitudinal direction of the tube for incision, the apparatus can be made compact so that it can be inserted into a body cavity as well as an opening together with an endoscope. Since the heating element, the inner hook and the laser light transmitting and irradiating means, which generate heat are housed in the outer hook in use or out of use for the treatment, they will not give any damages to the living tissue excepting for the tissue to be treated due to contact thereto.

In the second to sixth embodiments, it is preferable to use a handpiece similar to that of the first embodiment.

Figure 24:
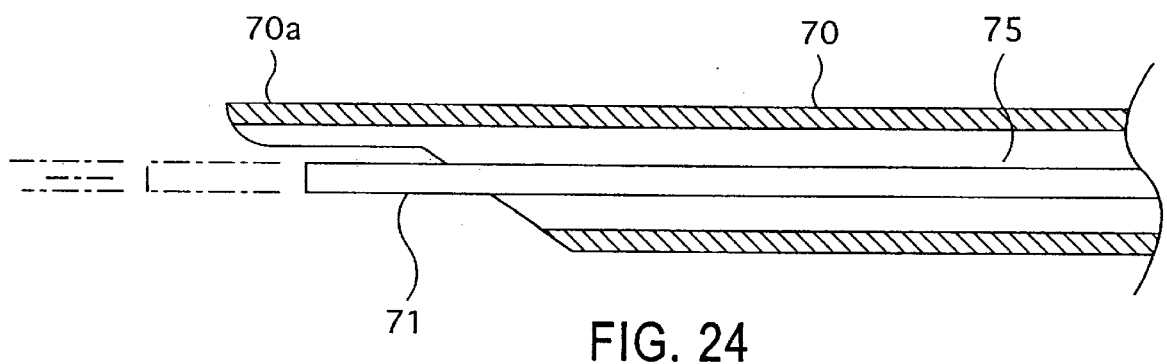
FIG. 24 is an enlarged longitudinal sectional view of main parts showing a seventh embodiment of the present invention.

FIG. 24 shows a seventh embodiment of the apparatus for medical treatment of the present invention. The apparatus includes an outer probe 70 including a hollow tubular member having a chisel blade like front end 70a which is formed integrally with the hollow tubular member by extending a part of the outer periphery of the member at the front end thereof in a longitudinal direction. The apparatus further includes a laser probe 71 serving as an inner probe comprising heating means for heating the target tissue to be treated which is inserted into the inside of the outer probe 70 and is extendable from the chisel blade like front end 70a by the operator's actuation. The outer probe 70 is preferably coated on the outer surface thereof with epoxy resin or ceramics to provide heat resistance and thermal induration.

The laser probe 71 may be of the type for heating the target tissue to be treated with the laser light from the front end of the laser probe 71. Accordingly, the laser probe 71 may be only an optical fiber.

Figure 25:
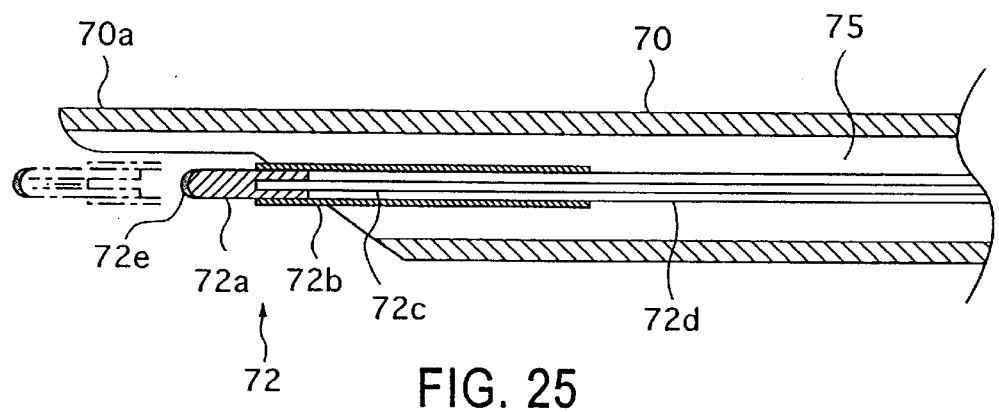
FIG. 25 is an enlarged longitudinal sectional view of main parts showing another form of laser prove.

Alternatively, a laser probe may be used comprising a light guide member 72a which is provided with a heating element 72e which generates heat on exposure to the laser light and laser light transmitting and irradiating means 72c (specifically an optical fiber) which is inserted into the hollow tubular member 72d and a sheath 72b and extends to the substantially intermediate position of the light guide member 72a in a longitudinal direction thereof in which the light guide member 72a is linked to the hollow tubular member 72d by the sheath 72b as shown in FIG. 25. In this case, it is only necessary to provide the heating element 73e at the front end of the probe if necessary.

Figure 26:
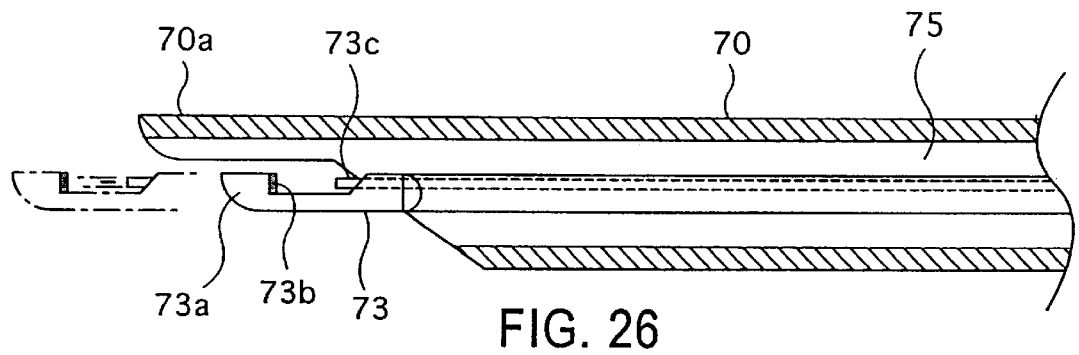
FIG. 26 is an enlarged longitudinal sectional view of main parts showing a further form of laser prove.
Figure 27:
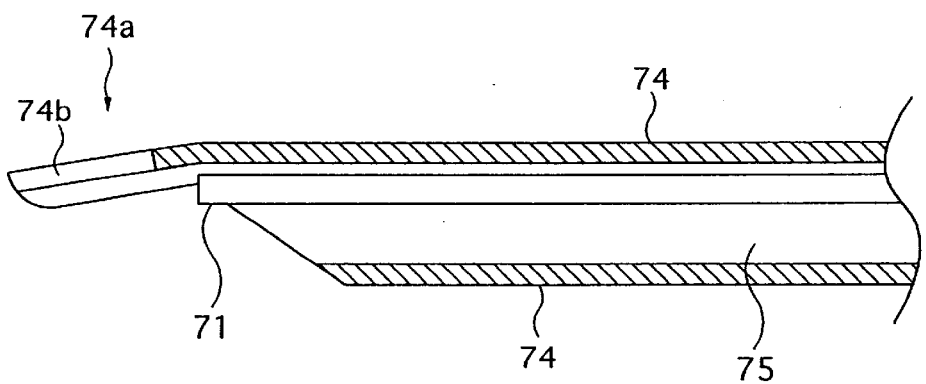
FIG. 27 is an enlarged longitudinal sectional view of main parts showing an eighth embodiment of the present invention.
Figure 28:
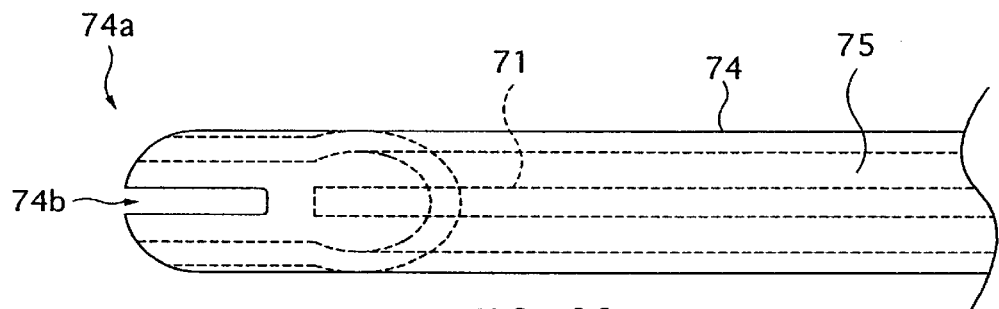
FIG. 28 is an upper face view of the eighth embodiment of the present invention.
Figure 29:
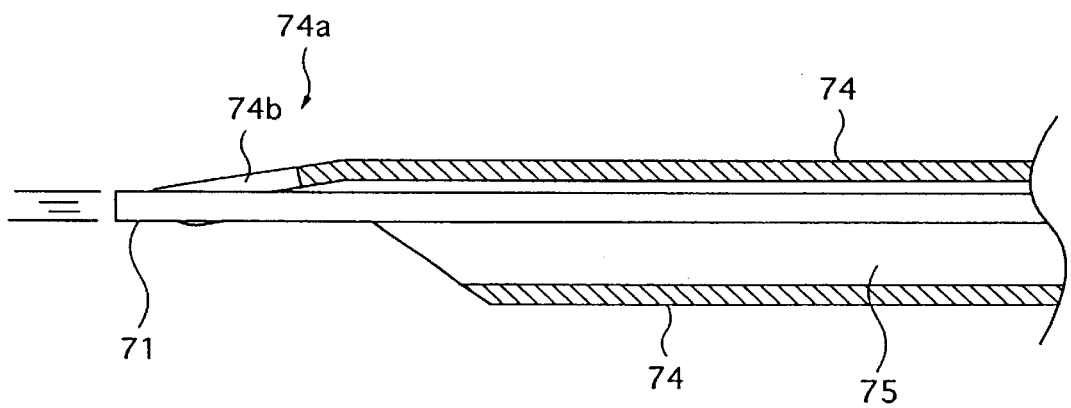
FIG. 29 is an enlarged longitudinal sectional view of main parts showing the laser light irradiation in eighth embodiment.

Another form of the laser probe as shown in FIG. 26 is proposed which comprises a trowel like probe 73 at the front end 73a thereof and a heating element 73b at the front end of the probe 73, which generates heats on exposure to the laser light. In the drawing, the heating element 73b is provided on the inner side of the trowel like front end 73a and laser light transmitting and irradiating means 73c which is inserted into the probe is disposed to face the heating element 73b.

In the seventh embodiment, for example, the embodiment shown in FIG. 24, incision of the living tissue is conducted by means of chisel blade like front end 73a of the outer probe 70 and solidification of the living tissue is conducted while the laser probe 71 is projected or not projected beyond the chisel blade like front end 70a according to needs. Local incision can be conducted with the laser light from the laser probe 71 depending upon the position of the target tissue.

The embodiments shown in FIGS. 25 and 26 are identical with that in FIG. 24 except that the treatment is conducted while the heating element 72e at the front end of the laser probe 72 and the front end 73a of the laser probe 73 in FIGS. 25 and 26 are projected beyond the chisel blade like front end 72a of the outer probe 70 to contact with the target tissue to be treated.

Another form of outer probe is proposed in which the chisel blade like front end 74a thereof is bent toward to the axis of the outer probe 74 and a notch 74b extending from the chisel blade like front end 74a to the substantial base end of the bent portion is provided (eighth embodiment).

Although any laser probes which have been described with reference to the seventh embodiment may be used in the eighth embodiment, it is particularly preferable to use the laser probe of the type in which for heating the target tissue to be treated by directing the laser light toward it from the front end of the laser probe. In this case, mechanical incision can be conducted simultaneously with the incision or solidification with the laser light from the laser probe 71 by forming the laser probe 71 in such a manner that the front end of the laser probe 71 faces the notch 74b of the front end of the outer probe 74. If localized incision is desired, the incision with a laser light from the laser probe 71 can be conducted as is similar to the above-mentioned seventh embodiment.

In the seventh and eighth embodiments, It is preferable to use the handpiece which has been described with reference to the foregoing first embodiment for conducting an operation of projecting the laser probes 71, 72, 73. Specifically, the outer probe and laser probe in the seventh embodiment are mounted on the handpiece in lieu of the outer hook probe and inner hook probe in the first embodiment.

Since the movement of the front end of the probe in incision operation of the apparatus for medical treatment in the seventh and eighth embodiments is conducted by only movement in an longitudinal direction of the probe, the apparatus can be miniaturized to such a size that the apparatus can be inserted into a body cavity together with an endoscope as well as an open position. Since the laser probe which is an inner probe having an heating element therein is housed in the outer hook, a damage due to the fact that the heated laser probe is brought into contact with the living tissue excepting a target tissue to be treated is substantially prevented. The seventh and eighth embodiments are preferable for the operation such as cosmetic surgery.

In seventh and eighth embodiments, it is preferable to form a gap 75 between the outer probe and the laser probe as shown in FIGS. 24 to 29 so that pumping of washing water, suction and discharge of the vaporized fume or material, or the blood can be conducted through the gap 75.

Figure 30:
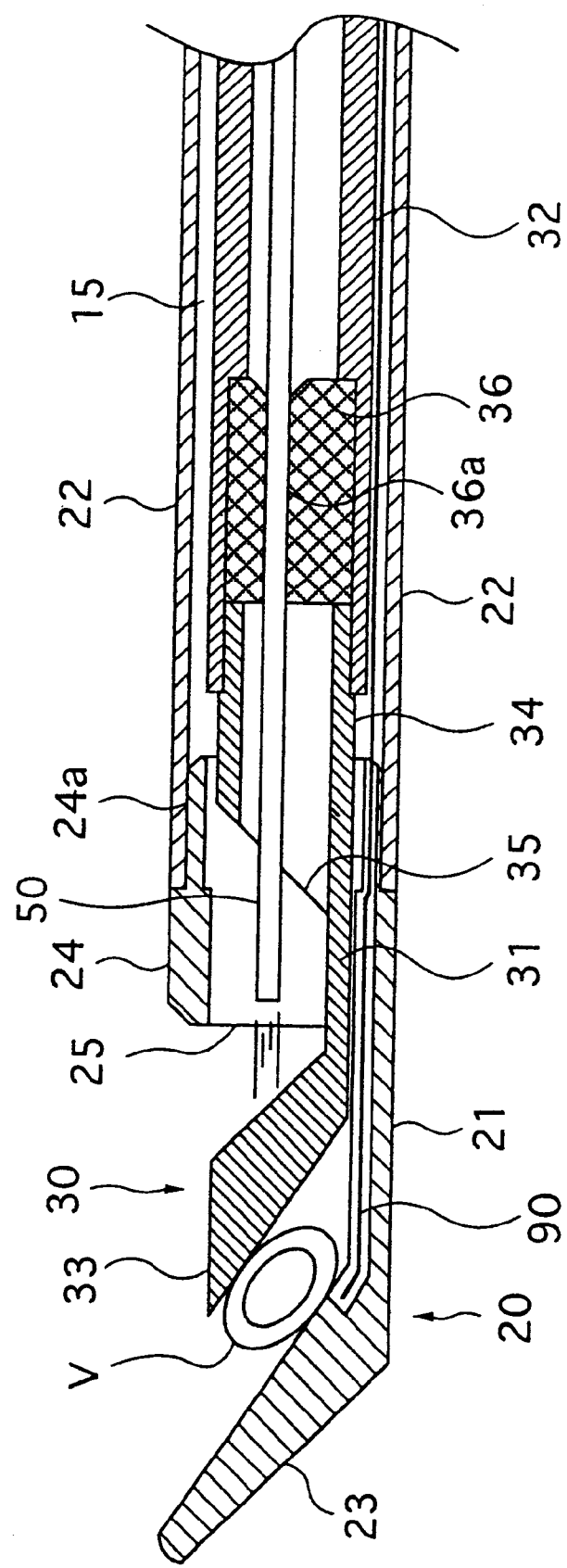
FIG. 30 is an enlarged longitudinal sectional view of main parts in the first embodiment of the present invention including a temperature sensor.

In the first to eighth embodiments, it is preferable to provide a temperature sensor at the front end of the apparatus if necessary. Specifically referring to the first embodiment, it is preferable to provide a temperature sensor 90, specifically a thermo-couple at a portion which will be close to the target tissue to be treated on the inner surface of the hook portion 23 of the outer hook 20 as shown in FIG. 30 since the temperature of the blood vessel V, the target tissue to be treated which is disposed between the outer hook 20 and the inner hook 30 can be monitored. Feedback of the result of monitor to the laser generator (not shown) allows the temperature of the target tissue to be adjusted to a value depending upon the purpose of the treatment. Particularly, the apparatus can be used for the treatment to provide a given heating pattern, for example, a treatment in which the target tissue to be treated is heated to a given temperature and its temperature is kept for a given period of time.

On the other hand, if the apparatus will be used for the incision or cutting of the target tissue to be treated, the surface of the outer probe and/or in a probe which will face to the object to be treated may be sharpened to enable the target to be cut.

Figure 31:
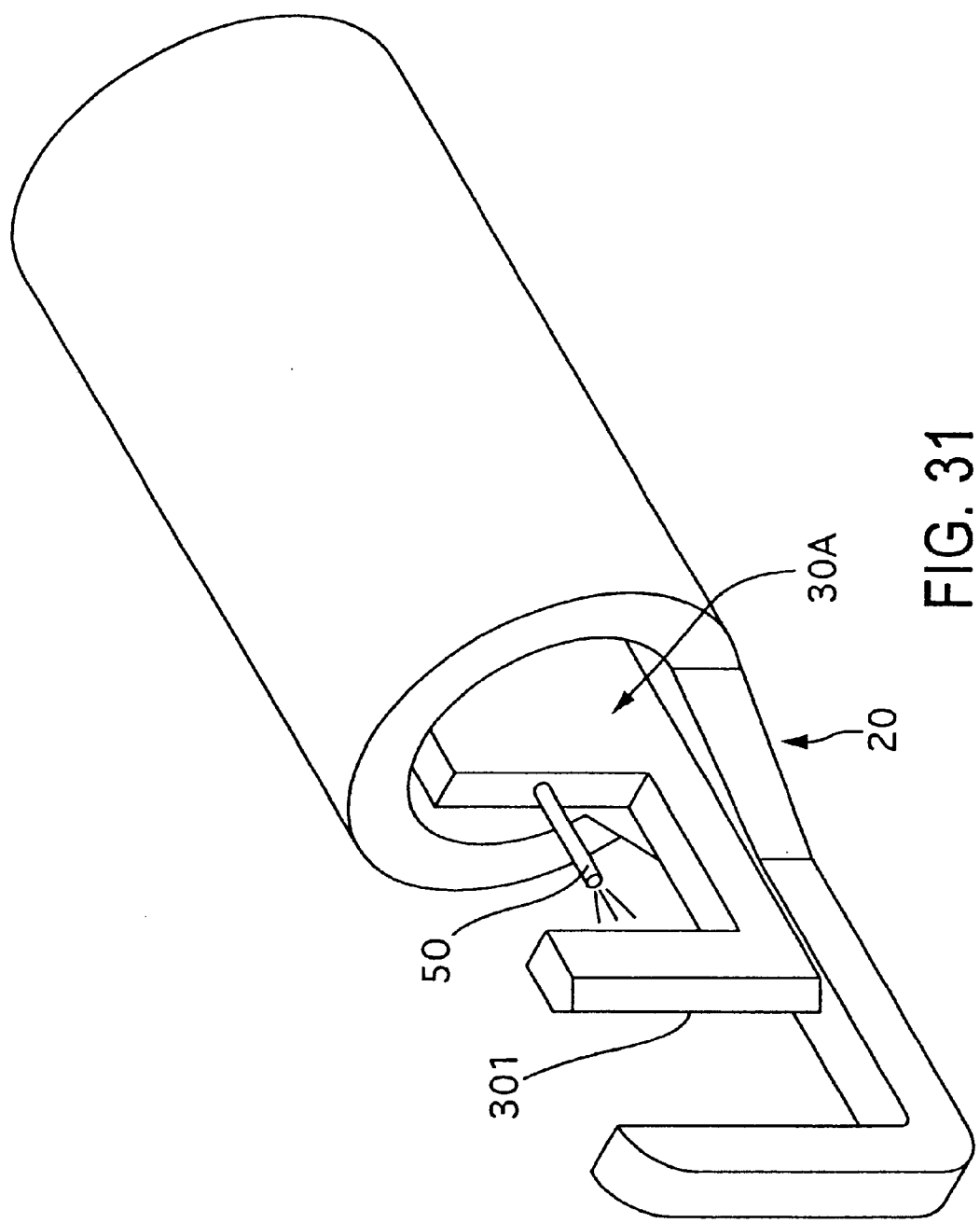
FIG. 31 is a schematic view showing a further embodiment of the present invention.
Figure 32:
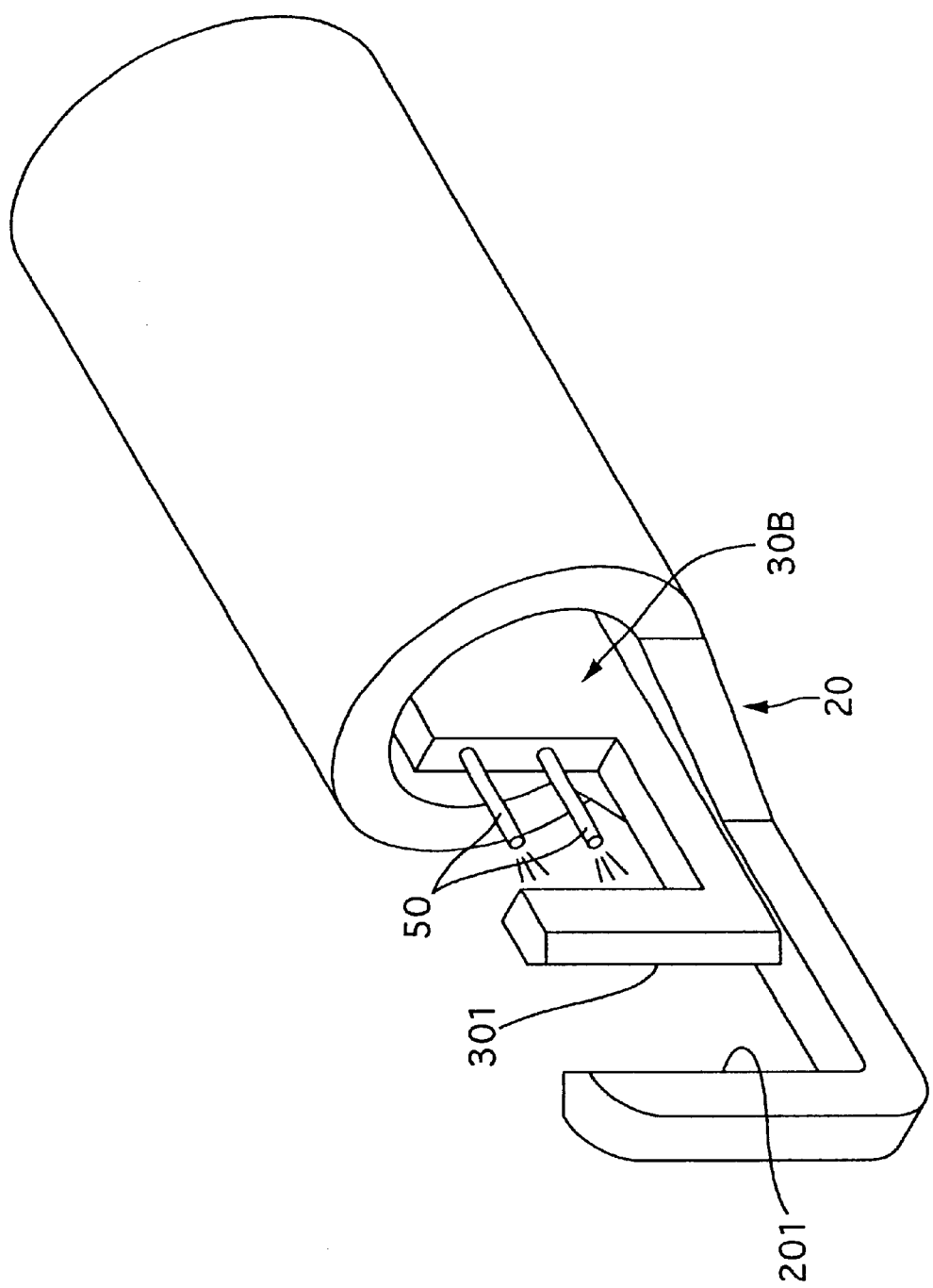
FIG. 32 is a schematic view showing a further more embodiment of the present invention.
Figure 33:
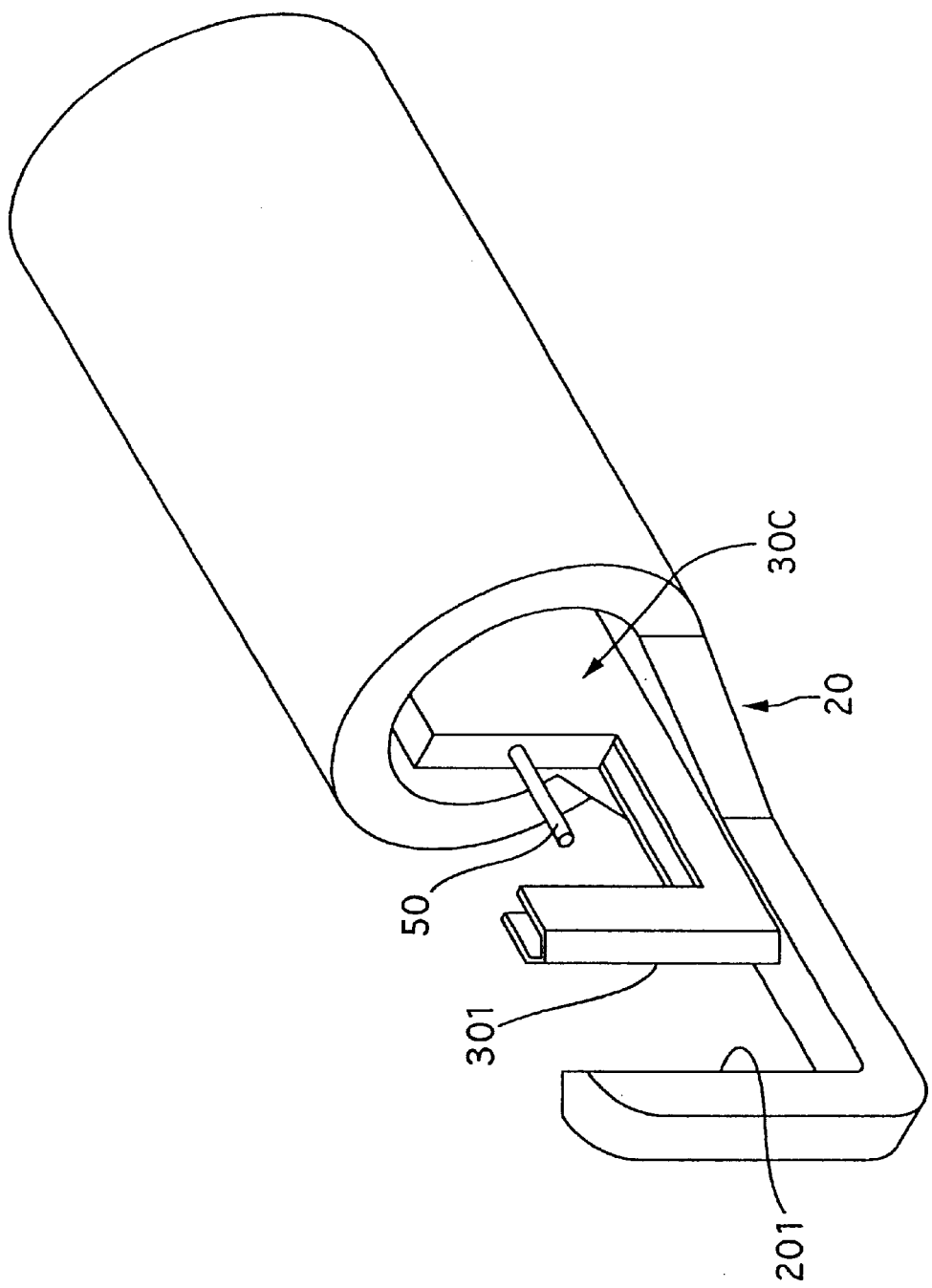
FIG. 33 is a schematic view showing a further more embodiment of the present invention.

For example, the front edge 301 of the inner probe 30a may be formed into an acute angle as shown in FIG. 31. The base end side 201 of the outer probe 20 may also be formed into an acute angle. In order to decrease the thermal capacity of the inner probe 30B, the inner probe 30C may be fabricated into the form of plate as shown in FIG. 33. This allows the temperature of the inner probe 30c to be quickly elevated when the irradiation with the laser light is started and to be quickly lowered when it is stopped.

Figure 34:
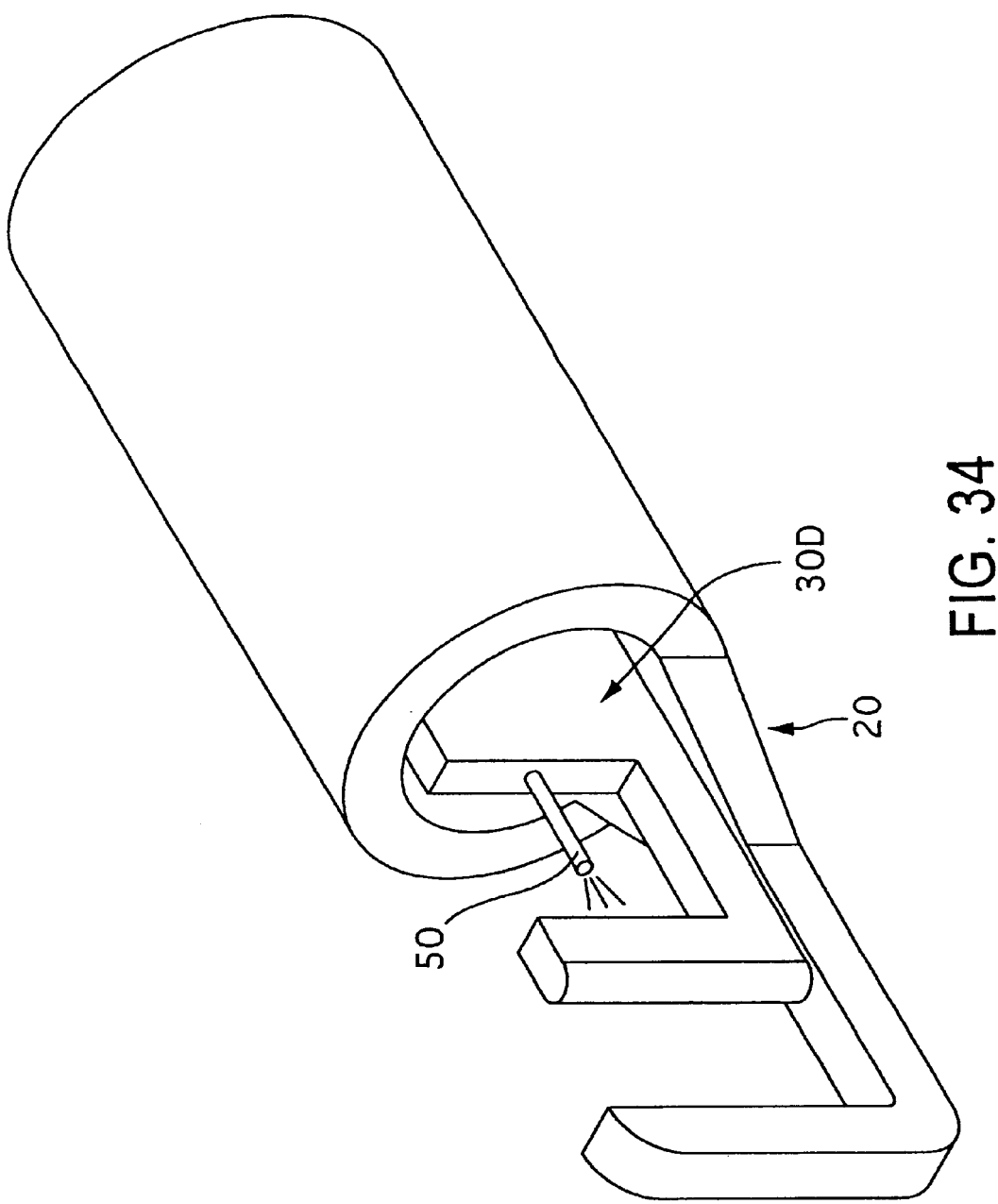
FIG. 34 is a schematic view showing a further more embodiment of the present invention.
Figure 35:
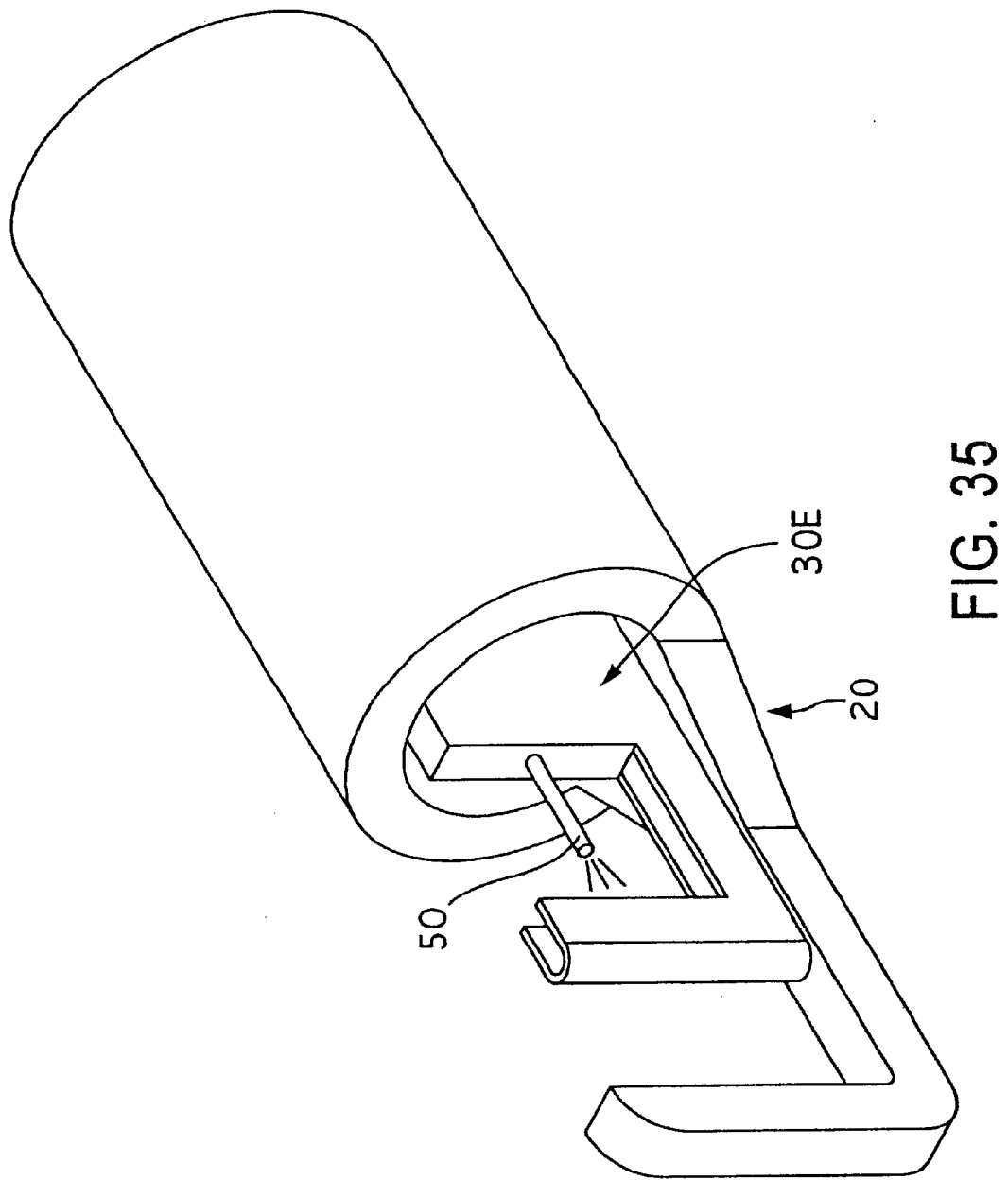
FIG. 35 is a schematic view showing a further more embodiment of the present invention.

If the apparatus will be used for solidifying the target tissue to be treated, an inner probe 30D and inner probe 30E having a curved outer surface as shown in FIGS. 34 and 35, respectively, may be used.

Figure 36:
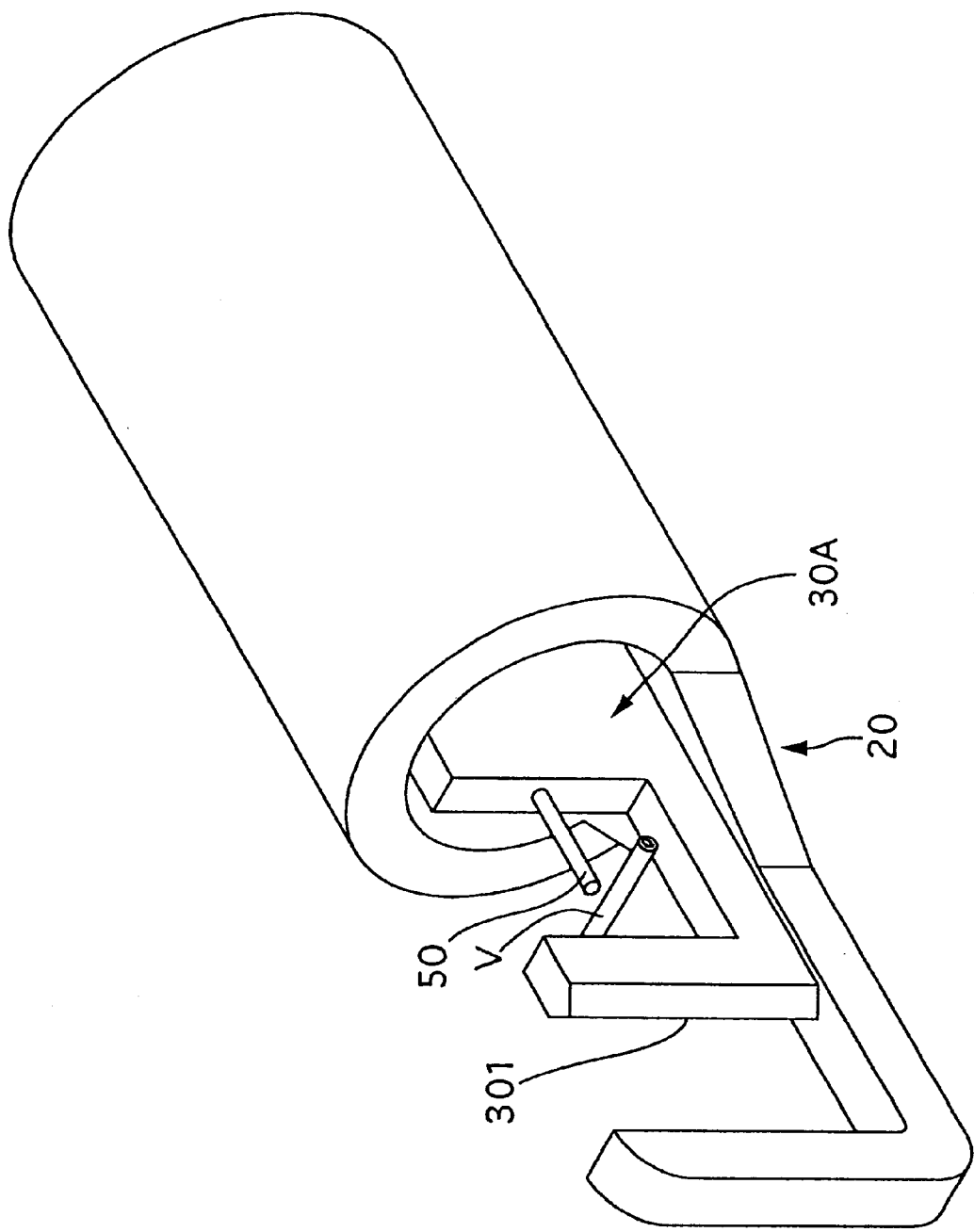
FIG. 36 is a schematic view showing another use of the present invention.

Each of the above-mentioned inner probes 30, 30A through 30E is in the form of hook. By forming the inner probe in the form of hook in such a manner, a target tissue to be treated such as a blood vessel V is located between the inner probe such as the inner probe 30A and an optical fiber 50 as shown in FIG. 36 so that the blood vessel can be burnt to cut by irradiation it with the laser light from the optical fiber 50 if necessary.

Figure 37:
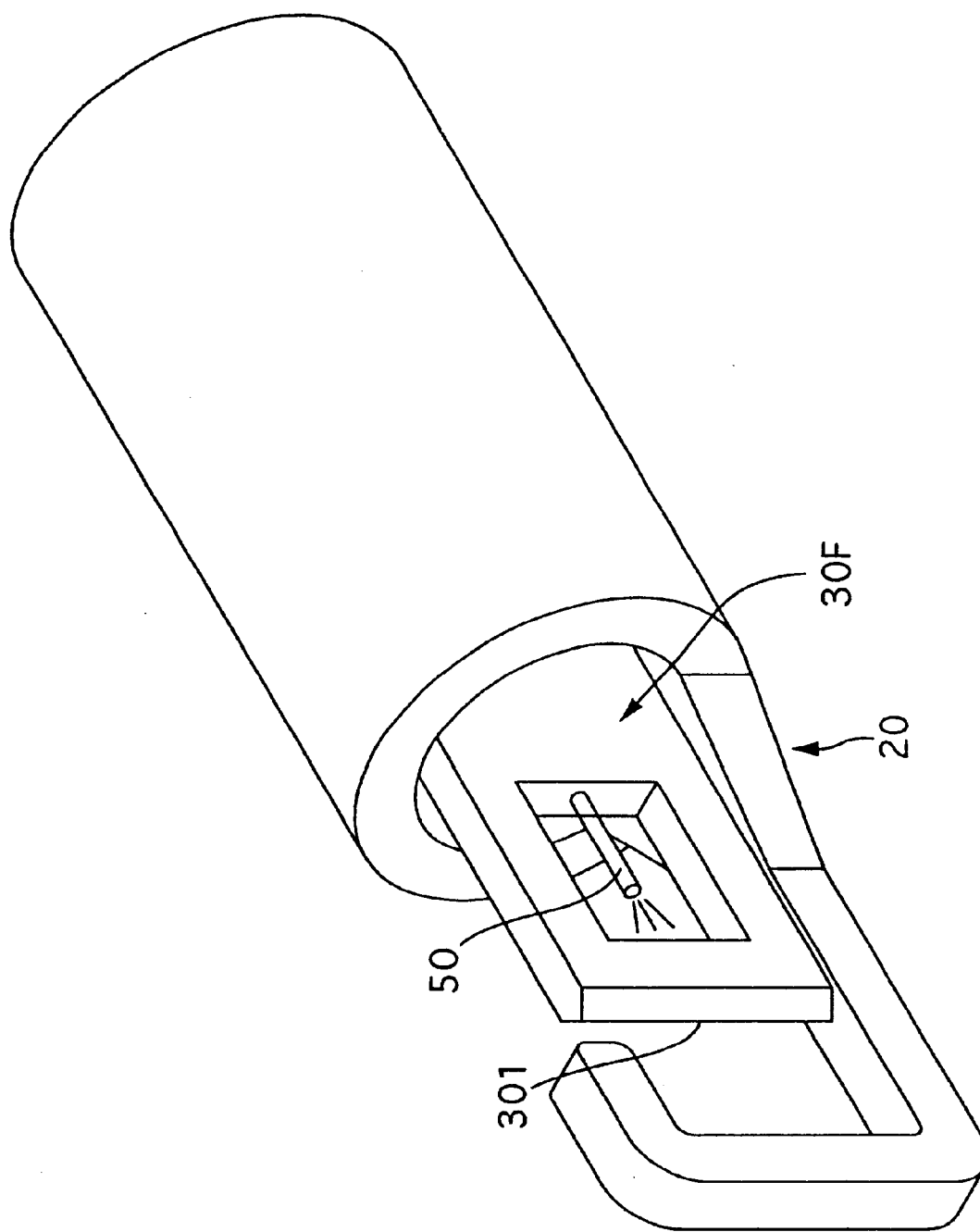
FIG. 37 is a schematic view showing a further more embodiment of the present invention.
Figure 38:
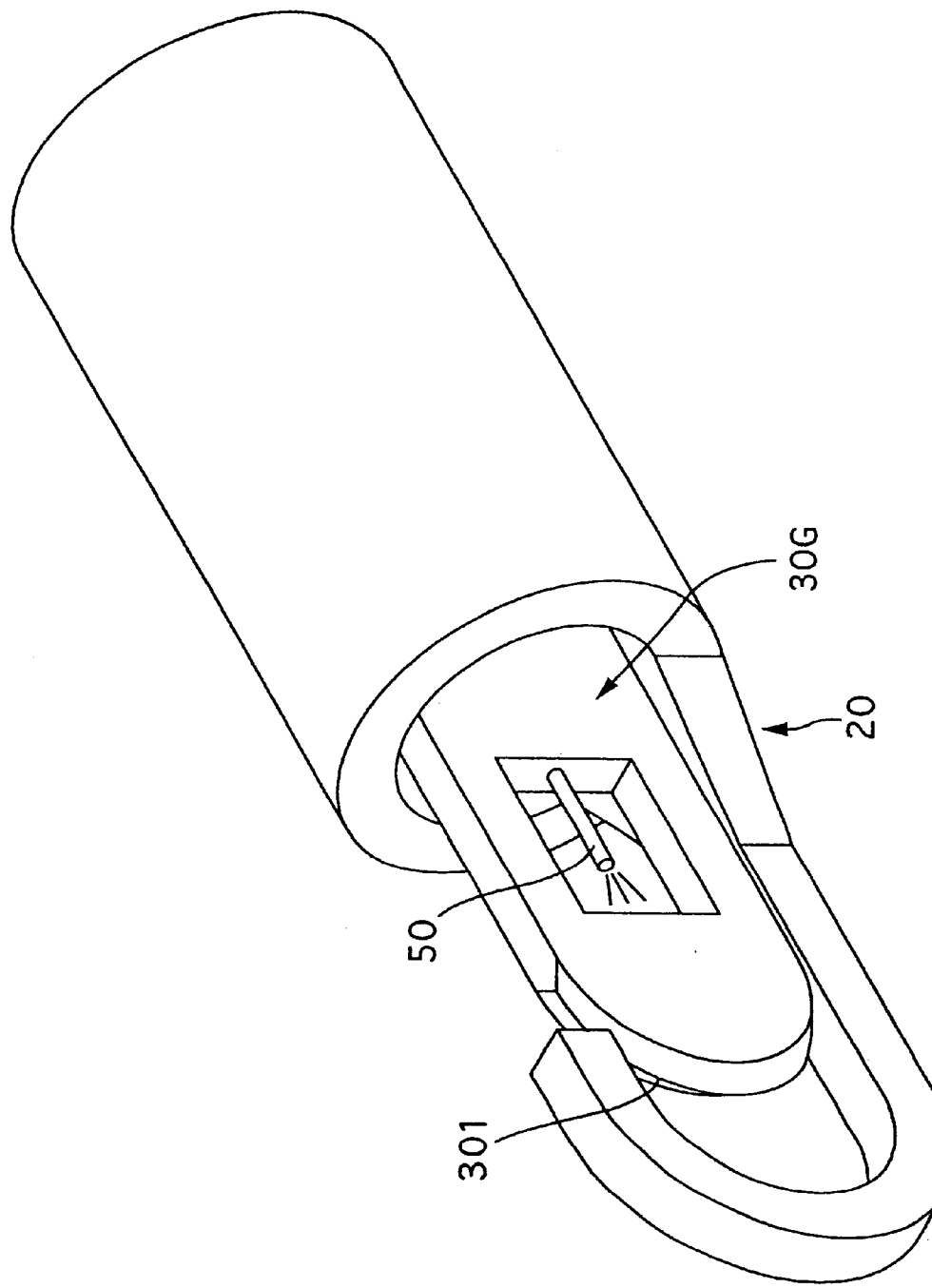
FIG. 38 is a schematic view showing a further more embodiment of the present invention.

On the other hand, an inner probes 30F and 30G which are not in the form hook and in which the front end portion of the optical fiber 50 is surrounded by a frame as shown in FIGS. 37 and 38 may be used. In this case, the side windows of the inner probe 30F and the inner probe 30G may not be opened but be closed.

Temperature detecting means may be connected to send inner probe and/or outer probe. For example, a temperature detecting lead may be embedded or extended along the outer probe so that its front end portion is extended to the hook portion of the outer probe or its vicinity and the base end of the temperature detecting lead is guided to the outside of the apparatus to be connected to the temperature detector. By doing this, the condition of heating of the target tissue to be treated is detected and is fed back for the control of the irradiation with the laser light.

The side of the inner which faces to the target tissue to be treated may be roughed by sandblasting if necessary and may be coated with a fluorine resin or gold to prevent the inner probe from being fused to the tissue.

The object of the present invention can be accomplished by making the inner probe of a material which per se generates heat on exposure to the laser light even if the inner probe is not formed with any heating element 33a and is exposed. As mentioned above, the present invention provides various advantages that incision of the tissue or hemostasis can be ideally achieved by one time operation and that the apparatus can be miniaturized to such a size that the apparatus can be inserted to a body cavity as well as an open position together with an endoscope and any damage to the living tissue other than the target tissue to be treated can be substantially prevented.

What is claimed is:

1. An apparatus for medical treatment, the apparatus comprising:

an outer probe in hook form;

heating means comprising a source of laser light; and an inner probe which is interposed between the heating means and the outer probe and which is moveable toward and away from the outer probe, the heating means being spaced from the inner probe and which selectively irradiates at least a portion of the inner probe from a predetermined distance.

2. The apparatus of claim 1, wherein the outer probe comprises a surface which faces a target tissue and wherein the inner probe comprises a surface which faces the target tissue, the surfaces being adapted to cut said target tissue.

3. The apparatus of claim 1, wherein the heating means irradiates the portion of the inner probe to heat the portion of the inner probe and to provide heat to a target tissue positioned between the inner probe and the outer probe.

4. An apparatus for medical treatment, the apparatus comprising:

an outer probe comprising a hollow tubular member in hook form at a front end thereof;

a heater element positioned on the hook form portion of an inner probe, the heater element adapted to absorb heatingly irradiated laser light;

heating means comprising a source of laser light; and, the inner probe comprising a hollow tubular member in hook form at a front end thereof, wherein the inner probe is interposed between the heating means and the outer probe and which is moveable toward and away from the outer probe, the heating means being spaced from the inner probe and which selectively and heatingly irradiates at least a portion of a target tissue positioned between the inner probe and the outer probe, the inner probe further comprising a source of laser light transmitting and irradiating means and a heater element.

5. The apparatus of claim 4, wherein the outer probe comprises a surface which faces a target tissue and wherein the inner probe comprises a surface which faces the target tissue, the surfaces being adapted to cut said target tissue.

* * * * *